(12) United States Patent
Krivoruk

(10) Patent No.: US 8,920,170 B2
(45) Date of Patent: Dec. 30, 2014

(54) ABUTMENT AND ABUTMENT SYSTEMS FOR USE WITH IMPLANTS

(75) Inventor: Anatoli Krivoruk, Philadelphia, PA (US)

(73) Assignee: Aeton Medical LLC, Philadelphia, PA (US)

( * ) Notice: Subject to any disclaimer, the term of this patent is extended or adjusted under 35 U.S.C. 154(b) by 0 days.

(21) Appl. No.: 13/401,349

(22) Filed: Feb. 21, 2012

(65) Prior Publication Data

US 2012/0214130 A1 Aug. 23, 2012

Related U.S. Application Data

(60) Provisional application No. 61/444,986, filed on Feb. 21, 2011, provisional application No. 61/500,399, filed on Jun. 23, 2011.

(51) Int. Cl.
*A61C 8/00* (2006.01)
(52) U.S. Cl.
CPC ............... *A61C 8/00* (2013.01); *A61C 8/0048* (2013.01); *A61C 8/0066* (2013.01)
USPC ............................ 433/173; 433/172; 433/174
(58) Field of Classification Search
USPC .......... 433/172–176, 218–223; 411/339, 402, 411/407, 408
See application file for complete search history.

(56) References Cited

U.S. PATENT DOCUMENTS

| | | |
|---|---|---|
| 3,793,728 A | 2/1974 | Corbineau |
| 4,281,991 A | 8/1981 | Michl et al. |
| 4,575,340 A | 3/1986 | Lustig |
| 4,622,011 A | 11/1986 | Malek |
| 4,657,510 A | 4/1987 | Gittleman |
| 4,681,542 A | 7/1987 | Baum |
| 4,722,688 A | 2/1988 | Lonca |
| 5,106,299 A | 4/1992 | Ghalili |
| 5,118,296 A | 6/1992 | Eldred |
| 5,195,891 A | 3/1993 | Sulc |
| 5,334,024 A | 8/1994 | Niznick |
| 5,344,457 A * | 9/1994 | Pilliar et al. .................. 606/60 |
| 5,417,570 A | 5/1995 | Zuest et al. |
| 5,674,073 A | 10/1997 | Ingber et al. |
| 5,685,715 A | 11/1997 | Beaty et al. |
| 5,759,036 A | 6/1998 | Hinds |

(Continued)

FOREIGN PATENT DOCUMENTS

| | | |
|---|---|---|
| EP | 0 438 984 A1 | 7/1991 |
| KR | 20-0306037 Y1 | 3/2003 |

(Continued)

OTHER PUBLICATIONS

"The Direct Abutment," Astra Tech Implants, brochure, undated, 4 pp., Astra Tech Inc., Lexington, USA.
"Simple Solutions Prosthetic Technique Manual," Rev B Mar. 2008, 24 pp., BioHorizons USA, Birmingham, USA.
"Can You Prevail in the Pursuit of Crestal Bone Preservation?," Certain® PREVAIL® Implant System, brochure, Rev C Mar. 2008, 8 pp., Biomet 3i™, Palm Beach Gardens, USA.
Östman, P., DDS, "NanoTite™ PREVAIL® Implants: Crestal Bone Preservation in the Aesthetic Zone," *Clinical Perspectives*, NanoTite™ Implant System, brochure, Jul. 2007, 7 pp., vol. 6, Issue 2, Biomet 3i™, Palm Beach Gardens, USA.

(Continued)

*Primary Examiner* — Yogesh Patel
(74) *Attorney, Agent, or Firm* — Jones Robb, PLLC

(57) ABSTRACT

An abutment for supporting a prosthesis relative to an implant includes an implant engaging portion configured to engage with a dental implant and a component supporting portion having a key feature on an external surface portion thereof. The key feature is configured to provide keyed mating engagement with a complimentary key feature on a component to be engaged with the abutment.

15 Claims, 16 Drawing Sheets

(56) References Cited

U.S. PATENT DOCUMENTS

| | | | |
|---|---|---|---|
| 5,762,500 A | 6/1998 | Lazarof | |
| 5,782,918 A | 7/1998 | Klardie et al. | |
| 5,823,776 A | 10/1998 | Duerr et al. | |
| 5,829,981 A | 11/1998 | Ziegler | |
| 5,904,483 A | 5/1999 | Wade | |
| 5,947,736 A | 9/1999 | Behrend | |
| 6,048,203 A | 4/2000 | Rosenberg | |
| 6,068,478 A | 5/2000 | Grande et al. | |
| 6,068,479 A | 5/2000 | Kwan | |
| 6,068,480 A * | 5/2000 | Misch et al. | 433/173 |
| 6,083,004 A | 7/2000 | Misch et al. | |
| 6,155,828 A | 12/2000 | Lazzara et al. | |
| D441,448 S | 5/2001 | Kumar | |
| 6,290,500 B1 | 9/2001 | Morgan et al. | |
| 6,299,447 B1 | 10/2001 | Zuest et al. | |
| 6,332,777 B1 | 12/2001 | Sutter | |
| 6,382,977 B1 | 5/2002 | Kumar | |
| 6,540,514 B1 | 4/2003 | Falk et al. | |
| 6,592,370 B2 | 7/2003 | Morgan | |
| 6,644,969 B2 | 11/2003 | Kumar | |
| 6,769,913 B2 | 8/2004 | Hurson | |
| 6,951,460 B2 | 10/2005 | Halldin et al. | |
| 6,981,871 B2 | 1/2006 | Mullaly et al. | |
| 7,014,464 B2 | 3/2006 | Niznick | |
| 7,066,736 B2 | 6/2006 | Kumar et al. | |
| 7,114,952 B2 | 10/2006 | Morgan | |
| 7,137,816 B2 | 11/2006 | Gervais et al. | |
| 7,163,398 B2 | 1/2007 | Klardie et al. | |
| 7,204,692 B2 | 4/2007 | Klardie et al. | |
| 7,207,800 B1 | 4/2007 | Kwan | |
| 7,207,801 B2 | 4/2007 | Vogt et al. | |
| 7,281,924 B2 | 10/2007 | Ellison | |
| 7,300,284 B2 | 11/2007 | Linder | |
| 7,309,231 B2 | 12/2007 | Engman | |
| 7,338,286 B2 | 3/2008 | Porter et al. | |
| 7,632,095 B2 | 12/2009 | Östman et al. | |
| 7,780,448 B2 | 8/2010 | Kim | |
| 8,075,313 B2 | 12/2011 | Ranck et al. | |
| 2001/0026913 A1 | 10/2001 | Xu et al. | |
| 2002/0177103 A1 | 11/2002 | Pelak | |
| 2003/0054319 A1 | 3/2003 | Gervais et al. | |
| 2003/0082499 A1 | 5/2003 | Halldin et al. | |
| 2003/0097906 A1 | 5/2003 | Shoher et al. | |
| 2003/0114553 A1 | 6/2003 | Karim et al. | |
| 2004/0101806 A1 | 5/2004 | Kumar et al. | |
| 2004/0101807 A1 | 5/2004 | Porter et al. | |
| 2004/0121287 A1 | 6/2004 | Morgan | |
| 2004/0185417 A1 * | 9/2004 | Rassoli | 433/173 |
| 2004/0241610 A1 | 12/2004 | Hurson | |
| 2005/0014108 A1 | 1/2005 | Wohrle et al. | |
| 2005/0136378 A1 | 6/2005 | Ennajimi et al. | |
| 2005/0136379 A1 * | 6/2005 | Niznick | 433/173 |
| 2006/0003290 A1 | 1/2006 | Niznick | |
| 2006/0084033 A1 * | 4/2006 | Gittleman | 433/173 |
| 2006/0121416 A1 | 6/2006 | Engman | |
| 2006/0147881 A1 | 7/2006 | Winter-Moore | |
| 2006/0172257 A1 | 8/2006 | Niznick | |
| 2006/0188844 A1 | 8/2006 | Dadi | |
| 2006/0204928 A1 | 9/2006 | Hurson | |
| 2006/0228672 A1 | 10/2006 | Hurson | |
| 2006/0246397 A1 | 11/2006 | Wolf | |
| 2006/0263747 A1 | 11/2006 | Hurson | |
| 2006/0286508 A1 | 12/2006 | Bassett et al. | |
| 2007/0015110 A1 | 1/2007 | Zhang et al. | |
| 2007/0031103 A1 | 2/2007 | Tinucci et al. | |
| 2007/0031793 A1 | 2/2007 | Casement et al. | |
| 2007/0059666 A1 * | 3/2007 | Zickman et al. | 433/173 |
| 2007/0281278 A1 | 12/2007 | Jorneus et al. | |
| 2007/0281279 A1 | 12/2007 | Chander | |
| 2008/0032263 A1 | 2/2008 | Bondar | |
| 2008/0096168 A1 | 4/2008 | Schonenberger | |
| 2008/0176186 A1 | 7/2008 | Schaub | |
| 2008/0206709 A1 | 8/2008 | Lannan | |
| 2008/0233539 A1 | 9/2008 | Rossler et al. | |
| 2008/0241792 A1 | 10/2008 | Rossler et al. | |
| 2009/0032989 A1 | 2/2009 | Karim et al. | |
| 2009/0123888 A1 | 5/2009 | Rosenberg | |
| 2009/0123891 A1 | 5/2009 | Rosenberg | |
| 2009/0305195 A1 | 12/2009 | Jones et al. | |
| 2010/0151420 A1 * | 6/2010 | Ranck | 433/173 |
| 2010/0151423 A1 | 6/2010 | Ranck et al. | |
| 2010/0159417 A1 | 6/2010 | Whipple | |
| 2010/0184002 A1 | 7/2010 | Ranck et al. | |
| 2010/0209877 A1 | 8/2010 | Hogan et al. | |
| 2010/0285427 A1 * | 11/2010 | Hung | 433/174 |
| 2011/0306014 A1 * | 12/2011 | Conte et al. | 433/173 |
| 2012/0135370 A1 | 5/2012 | Ranck et al. | |

FOREIGN PATENT DOCUMENTS

| | | |
|---|---|---|
| KR | 2003-0030549 | 4/2003 |
| KR | 10-0693806 B1 | 5/2006 |
| KR | 10-0799368 B1 | 1/2008 |
| WO | WO 03/030768 A1 | 4/2003 |
| WO | WO 2008/060565 A2 | 5/2008 |
| WO | WO 2008/093994 A1 | 8/2008 |
| WO | WO 2010/068552 A2 | 6/2010 |
| WO | WO 2010/083393 A2 | 7/2010 |
| WO | WO 2010/093737 A2 | 8/2010 |
| WO | WO 2011/156668 A2 | 12/2011 |

OTHER PUBLICATIONS

Lazzara, R. J., DMD, MScD, "Clinical Indications Demonstrating Bone Preservation with The Certain® PREVAIL® Implant," *Clinical Indications*, Certain® PREVAIL® Implant System, brochure, REV A Feb. 2007, 12 pp., Biomet 3i™, Palm Beach Gardens, USA.

"XP1 Transmucosal Implant System," [website page online]. Keystone Dental, Inc., [retrieved Mar. 3, 2009], Retrieved from the Internet: <URL: http://www.keystonedental.com/implants/xp1>.

"Cement-Retained Crowns and Bridges with the Solid Abutment System," catalog, Jan. 2008, 27 pp, Straumann, Basel, Switzerland.

"Immediate Temporary & QuickTemp™ Abutments—Temporary Solutions," catalog, 2007, 4 pp., Nobel Biocare Services AG.

"SPI®System—Design Concept," brochure, May 2005, 28 pp., THOMMEN Medical AG, Waldenburg, Switzerland.

"SPI®Easy—Prosthetic Procedure," brochure, Nov. 2006, 28 pp., THOMMEN Medical AG, Waldenburg, Switzerland.

"Restorative Manual," OSSEOTITE® Certain® Implant System and OSSEOTITE® External Hex Connection System, brochure, Rev B Nov. 2007, 32 pp., Biomet 3i™, Palm Beach Gardens, USA.

"Basic Information on the Surgical Procedure," manual, Jan. 2007, 64 pp., Straumann, Basel, Switzerland.

"Basic Information on the Surgical Procedures," manual, Sep. 2007, 79 pp., Straumann, Basel, Switzerland.

Carol Murphy, DentalTown Magazine, Apr. 2002, pp. 10-18, see p. 14, line 7-9.

International Search Report dated Sep. 19, 2012 for corresponding International Application No. PCT/US2012/025946.

Written Opinion of the International Search Authority dated Sep. 19, 2012 for corresponding International Application No. PCT/US2012/025946.

English language abstract of KR 2003-0030549, [retrieved Feb. 23, 2011], Retrieved from the Internet: <URL: http://v3.espacenet.com>.

English language abstract of KR 10-0693806 Bl, [retrieved Oct. 27, 2010], Retrieved from the Internet: <URL: http://v3.espacenet.com>.

English language abstract of KR 10-0799368 B1, [retrieved Oct. 27, 2010], Retrieved from the Internet: <URL: http://v3.espacenet.com>.

English language abstract of KR App. No. 20-0306037Y1, [retrieved Feb. 24, 2011], Retrieved from the Internet: <URL: http://translate.google.com>.

* cited by examiner

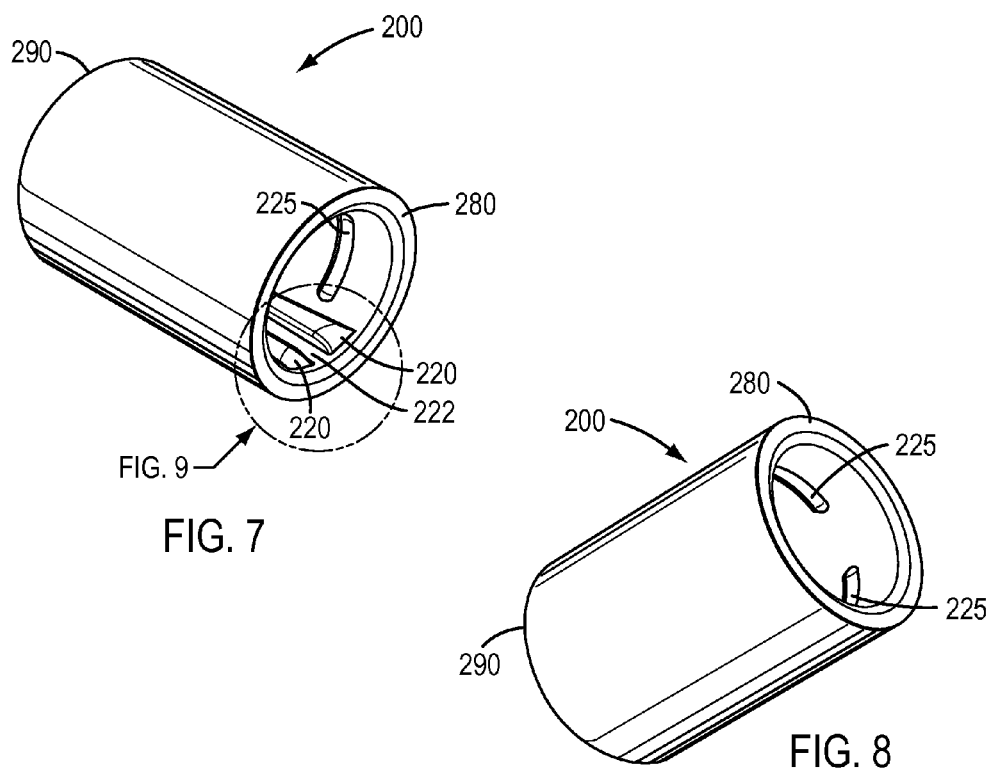
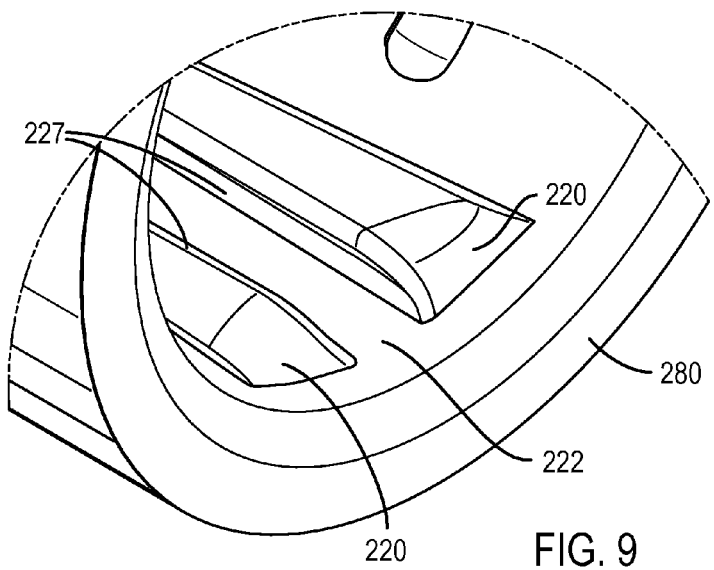

ABUTMENT AND ABUTMENT SYSTEMS FOR USE WITH IMPLANTS

CROSS-REFERENCE TO RELATED APPLICATIONS

This application claims the benefit of U.S. Provisional Patent Application No. 61/444,986, filed Feb. 21, 2011, and U.S. Provisional Patent Application No. 61/500,399, filed Jun. 23, 2011, the entirety of each of which is incorporated herein by reference.

TECHNICAL FIELD

The present teachings relate to components used with implants configured to be implanted in a patient's body, for example, in bone and/or cartilage. For example, the present teachings relate to components used with dental implants for supporting and retaining replacement teeth (e.g., temporary and/or permanent restorations). By way of particular example, the present teachings relate to abutments and components, such as, for example, copings, for mating with such abutments.

INTRODUCTION

Implants placed in bone and/or cartilage represent a growing field of reconstruction technology for replacing parts of the body, for example, with prosthetic parts. Such implants may be secured in the bone and/or cartilage and used to anchor a prosthetic body part in position.

One type of implant that has relatively widespread use includes dental implants. During dental implantation, a hole is drilled through the gingiva, the gums surrounding the root of a tooth, and/or into the jawbone. An implant, which may be, for example, made of titanium or titanium alloy, is then fixed within the hole of the jawbone. Over a period of months, the titanium implant fuses to the jawbone through a process called osseointegration. After a period of time, ranging from weeks to months, a permanent replacement tooth (sometimes referred to a final restoration or permanent restoration) is secured relative to the implant in the patient's mouth. Prior to placement of the permanent replacement tooth, a patient may also have a temporary replacement tooth (sometimes referred to as a temporary restoration) secured relative to the implant to provide some function and aesthetics in the time period before the permanent replacement tooth is in place.

For placing a temporary tooth, a so-called temporary coping is engaged with the implant, for example, via an abutment in the patient's mouth and a material (such as, for example, an acrylic material) used to create a temporary tooth is bonded thereto. This process can be done either chairside by the dentist or in a dental laboratory. Some adjustments may be made to the height, angle, and/or inter-occlusal clearance of the portion of the abutment that supports the restoration if necessary, for example, by using a bur to shave the abutment. In some approaches, a plastic temporary coping designed to provide a mechanical bond, for example, via cement or other adhesive, with the veneering material is placed over the abutment or a dental analog. Again, adjustments for inter-occlusal height, clearance, and/or angle of the temporary restoration may be made if necessary. Prefabricated polycarbonate crowns or vacuum stents also are used with a veneering material to complete fabrication of the temporary restoration.

In some conventional techniques, to assist in orienting a component, such as, a coping for example, to be supported by the abutment, conventional abutments generally have a flat surface portion on an external surface that is configured to mate with a corresponding flat surface portion on an internal surface of the component, such as, for example, a temporary or permanent coping (i.e., prior to securing, the coping is rotated relative to the abutment to align the respective flat portions). To prevent relative rotational movement, the flat portions on the abutment and coping must provide a precise mating fit with each other with very low tolerances for error between the overall configuration and dimensions of the two flat surface portions. Manufacturing the flat portions to such tolerances, however, can be difficult to achieve. If a precise mating fit of the two flat surface portions is not achieved, at least some rotation of the coping relative to the abutment, and consequently the prosthesis within the patient's mouth, can occur. Further, when placing a coping or other component relative to the abutment, it can be difficult for a dental practitioner or other user to determine whether the flat surfaces are precisely aligned, which can lead to improperly orienting and seating the component on the abutment. Such improper seating and orientation can lead to damage of the prosthesis, the abutment, and/or possibly the implant, and potentially to the patient (e.g., causing tissue recession), if for example, the finish line of the component on the abutment relative to the implant and/or abutment is not precise and a gap is present.

It may be desirable, therefore, to provide an abutment configuration that can achieve a precise mating and improved mechanical engagement with components (e.g., copings) supported thereon. It may be desirable to provide an abutment that can minimize errors associated with orienting and seating of a component on the abutment. It may be further desirable to provide an abutment that facilitates properly orienting and seating of a component, such as a coping, on the abutment, while also substantially preventing relative rotation between the component and the abutment.

It also may be desirable to provide a system that improves the accuracy and precision of the fit of a temporary replacement tooth structure, e.g., with an abutment and implant.

SUMMARY

The present teachings may satisfy one or more of the above-mentioned desirable features and/or solve one or more of the above-mentioned problems. Other features and/or advantages may become apparent from the description that follows.

In accordance with various exemplary embodiments of the present teachings, an abutment for supporting a prosthesis relative to an implant includes an implant engaging portion configured to engage with a dental implant and a component supporting portion having a key feature on an external surface portion thereof. The key feature is configured to provide keyed mating engagement with a complimentary key feature on a component to be engaged with the abutment.

In accordance with various additional exemplary embodiments of the present teachings, a system for securing a coping within a patient's body includes an abutment comprising an implant engaging portion configured to engage with a dental implant and a component supporting portion having a key feature on an external surface portion thereof. The system further includes a coping having a complimentary key feature on an internal surface portion. The key feature and the complimentary key feature are configured to provide a keyed making engagement of the coping and the abutment.

Additional objects and/or advantages of the present teachings will be set forth in part in the description which follows, and in part will be obvious from the description, or may be learned by practice of the present teachings. Those objects and advantages may be realized and attained by means of the elements and combinations particularly pointed out in the appended claims.

It is to be understood that both the foregoing general description and the following detailed description are exemplary and explanatory only and are not restrictive of the present teachings or claims. Rather, the claims are intended to cover a broad scope, including equivalents.

The accompanying drawings, which are incorporated in and constitute a part of this specification, illustrate exemplary embodiments of the present teachings and together with the description, serve to explain certain principles.

BRIEF DESCRIPTION OF THE DRAWINGS

FIG. 7 is a perspective view from an apical end of an exemplary embodiment of a temporary coping in accordance with the present teachings;

FIG. 8 shows an additional perspective view of the temporary coping of FIG. 7;

FIG. 9 shows a detailed view of a key feature of FIG. 7;

DETAILED DESCRIPTION OF VARIOUS EXEMPLARY EMBODIMENTS

Figure 1:
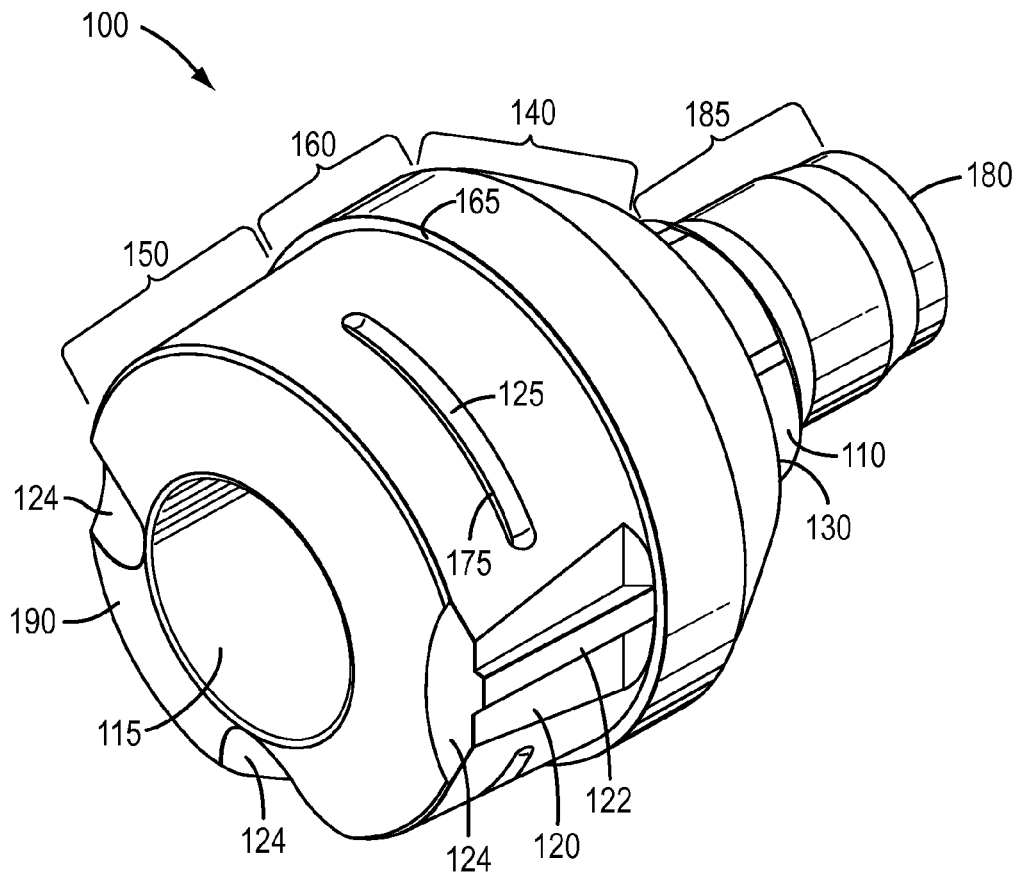
FIG. 1 is a perspective view from the coronal end of an exemplary embodiment of an abutment in accordance with the present teachings.

Reference will now be made in detail to various exemplary embodiments of the present teachings, examples of which are illustrated in the accompanying drawings. Wherever possible, the same reference numbers will be used throughout the drawings to refer to the same or like parts.

The present teachings contemplate systems and components thereof useful for securing prostheses relative to implants, such as, for example, securing tooth restorations relative to a dental implant. It is contemplated that various exemplary embodiments of the present teachings may comprise an abutment used in conjunction with various copings employed in the implantation process (e.g., impression copings, temporary copings, and/or permanent copings or frameworks), wherein the abutment is engaged with the implant to support and secure (at least temporarily) the coping within a patient's mouth.

It is further contemplated that the various components may be used in conjunction with various implant configurations, such as conventional implant configurations that include but are not limited to, for example, various Tissue and Bone Level Implants made by ITI Straumann; Solid Screw and Tapered Effect Implants made by ITI Straumann, including but not limited to the 4.1 mm and 4.8 mm Solid Screw and Tapered Effect Implants, and the 4.8 mm Wide Neck Solid Screw Implant and Tapered Effect Implant; Keystone Stage-1 and XP Implants; BlueSky Bio One Stage Implant with Regular and Wide Platform and BlueSky Bio Trilobe and Internal Hex System Implants; SS Implant and Excellent Solid Implant, 3I Tapered and Parallel Walled Implants; Zimmer's Tapered ScrewVent, Tapered SwissPlus, and Spline Implants; and Astra's Osseospeed TX Profile and TX with Tapered Apex Implants, among others. Implants with which various exemplary embodiments are configured to be used may also include a variety of coronal configurations for mating with abutments in accordance with the present teachings, including, but not limited to, for example, tapered internal coronal necks (e.g., conically-tapered internal coronal necks) and/or indexed (e.g., polygonal) anti-rotational internal coronal neck features, with which those having ordinary skill in the art are familiar. Those having ordinary skill in the art will appreciate a wide variety of conventional implants and other implant structures with which the various components in accordance with the present teachings may be utilized. Thus, the implant mating portions described and depicted in the exemplary embodiments herein are exemplary only and not intended to be limiting of the scope of the present teachings or claims; rather, those of ordinary skill in the art would understand how to modify the implant mating portion of the abutment to configure the same to mate with a variety of differing implant configurations.

In various alternative exemplary embodiments, abutments in accordance with the present teachings may be formed integrally as a single-piece structure with the implant rather than being formed as a separate engageable component.

In accordance with various exemplary embodiments, to precisely align and secure a component (e.g., coping) to an abutment within a patient's mouth, the present teachings contemplate an abutment for engaging a dental implant that includes a component supporting portion having a feature on an external surface portion thereof configured for keyed mating engagement with the component. In various exemplary embodiments, for example, an abutment may include a component supporting portion having a flat surface portion and a relief feature extending along at least a portion of a length of the flat surface portion. In various exemplary embodiments, therefore, when assembled with, for example, a coping, the relief feature can engage a corresponding, complimentary relief feature on the coping to prevent rotation of the coping (and tooth prosthesis) relative to the abutment.

In various exemplary embodiments, therefore, abutments of the present teachings provide a "key feature" to promote proper orientation and alignment of a coping, or other component, thereon and to provide a keyed mating engagement with such component to substantially prevent relative rotation of the coping and abutment once mated together.

As used herein, the terms "key feature," and the like can refer to one or more relief features, such as, male relief features, including, for example, protrusions, ridges, etc., and/or female relief features, including, for example, grooves, slots, recesses, etc., that are configured to mate with corresponding, complimentary relief features to secure together structural components via a keyed mating engagement. A "keyed mating engagement" and variations thereof refers to engaging or securing two components to each other in a manner that generally permits relative axial movement between the two components but prevents relative rotational movement between the two components. As used here, the term "key feature" is intended, therefore, to refer to one or more of such structures that can be either keys, keyways, or a combination of keys and keyways (as those terms are used by those having ordinary skill in the art to describe structures that provide keyed mating engagement between components). Thus, in various exemplary embodiments, a key feature on an abutment can include one or more male or female relief features (or combinations thereof) that are configured to provide a keyed mating engagement with one or more complimentary male or female relief features (or combinations thereof) on a component to be supported and engaged with the abutment to prevent relative rotation of the same.

In accordance with various additional exemplary embodiments, the abutment may also include one or more retention features (e.g., grooves) on an outer peripheral surface (e.g., an outer lateral surface) thereof, which are configured to engage with one or more corresponding retention features (e.g. protrusions) on a coping in order to achieve mechanical securing, for example, via a snap-fit engagement, of a restoration to the abutment, for example, without requiring the use of cement or other bonding mechanism. Such retention features are configured to prevent relative axial movement of the component relative to the abutment, at least when a force tending to move the component axially relative to the abutment is below a threshold amount. The present teachings additionally contemplate, for example, abutments having a plurality of retention features (e.g., grooves) substantially transversely oriented and spaced from one another around a peripheral external surface of the abutment and disposed at substantially the same axial location along a length of the abutment. Partial retention features, as opposed to a single continuous retention feature that extends around substantially the entire peripheral surface of the abutment between edges of a flat surface portion, for example, may require less force to disengage a temporary coping from the abutment for subsequent application of a permanent restoration.

The drawings included herewith as part of the specification contain various dimensions, tolerances, and/or other specifications that are not intended to be limiting of the present teachings or the scope of the invention herein. Rather, the dimensions, tolerances, and/or other specifications noted on the drawings represent an exemplary embodiment of the various components depicted. Those having ordinary skill in the art would understand that modifications to such dimensions, tolerances and/or other specifications may be made as desired and in accordance with the present teachings without departing from the scope of the present teachings.

As used herein, those having ordinary skill in the art are familiar with the meaning of the terms "apical" and "coronal." As used herein, "apical" refers to a direction toward the jaw bone, or toward root tips of teeth. If the term "apical" is used to refer to a portion of a component, it refers to the portion of the component that would be facing, closer to, and/or in a direction of the jaw bone and/or root tips if the component were placed in an operational position in a patient's mouth. The term "coronal" refers to a direction opposite the jaw bone and toward the crowns of teeth. If the term "coronal" is used to refer to a portion of a component, it may refer to the portion of the component that would be facing, closer to, and/or in direction of the crown portion of teeth if the component were placed in an operational position in a patient's mouth.

Figure 2:
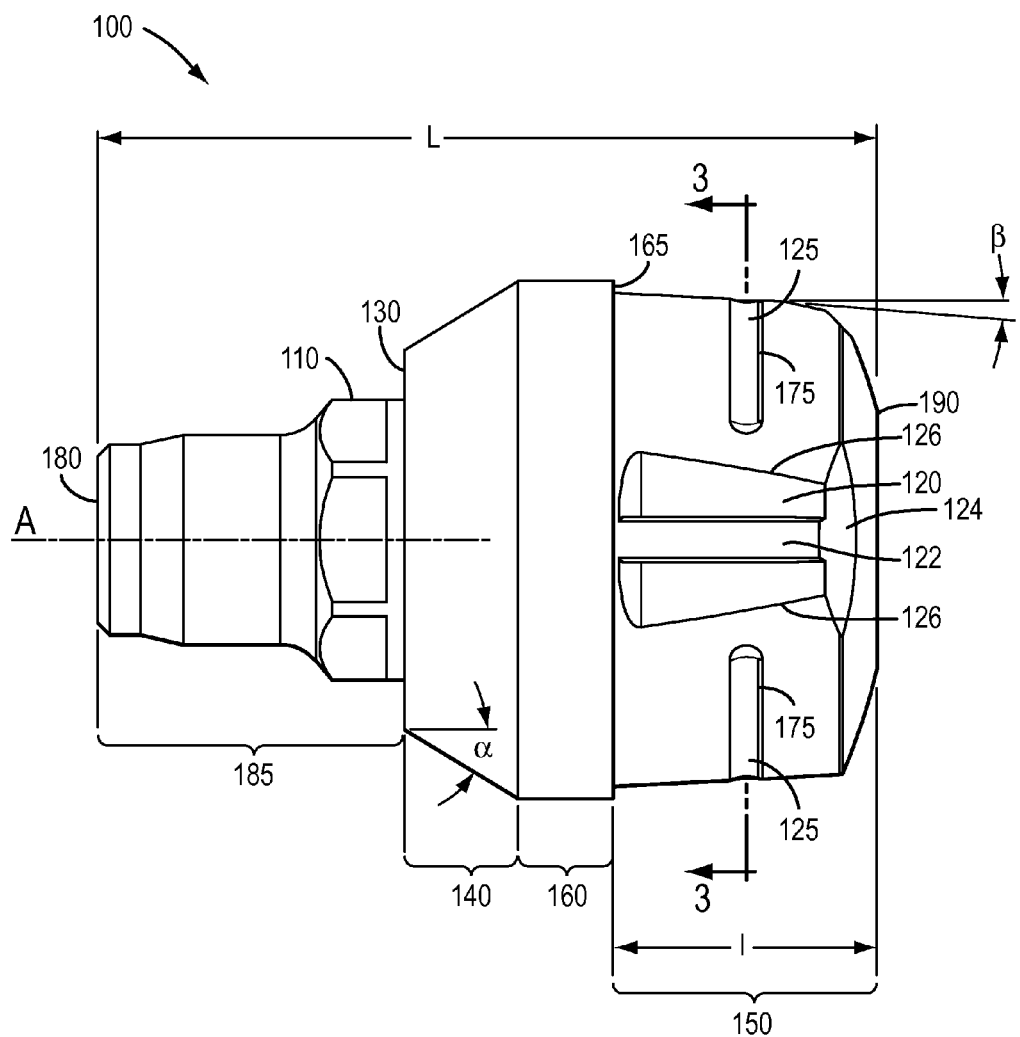
FIG. 2 is a side view of the abutment of FIG. 1.
Figure 15:
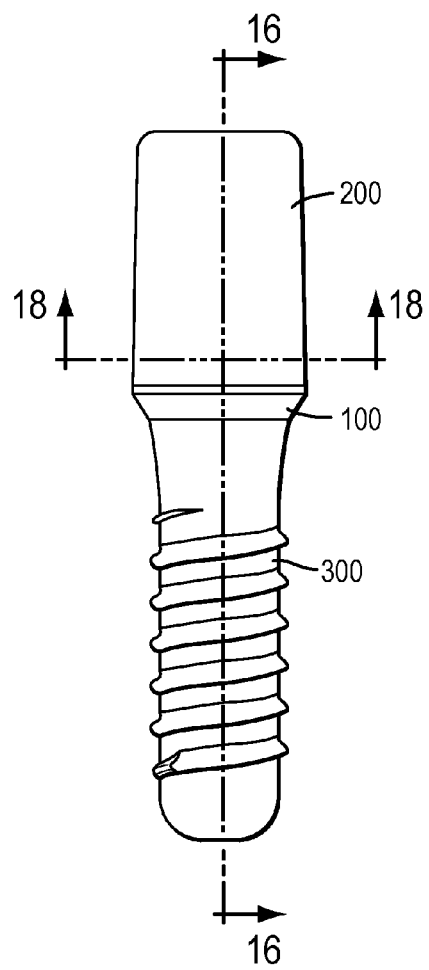
FIG. 15 is a side view of the temporary coping of FIG. 7 engaged with the abutment of FIG. 1, wherein the abutment is engaged with an implant in accordance with the present teachings.
Figure 16:
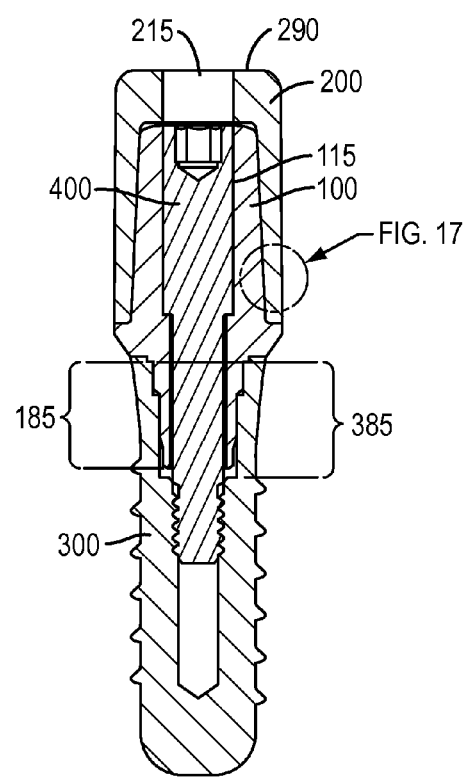
FIG. 16 is a cross-sectional view of the assembly of FIG. 15 taken through line 16-16 of FIG. 15.
Figure 17:
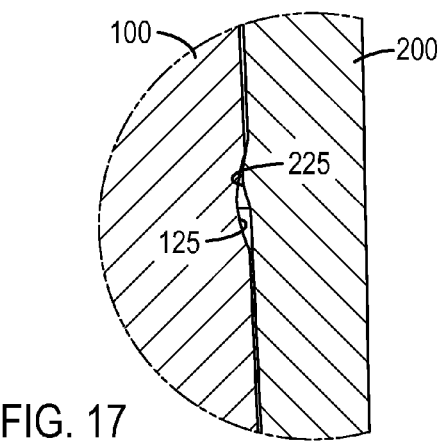
FIG. 17 shows a detailed view of a protrusion mated with a retention groove in FIG. 16.

With reference now to FIGS. 1 and 2, one exemplary embodiment of an abutment 100 for use with a dental implant (e.g., a dental implant 300 as illustrated in FIGS. 15 and 16) is depicted. The abutment 100 includes an implant (or apical) end 180 that engages with the implant and a coronal end 190 that receives a component (such as, e.g., a temporary coping described further below and/or other components which those of ordinary skill in the art would have familiarity) configured to be secured to the abutment 100. The abutment 100 may further include an implant engaging post 185 that includes the apical end 180 and an anti-rotational portion 110 configured to fit within a similarly configured opening in a dental implant. In the exemplary embodiment shown, the anti-rotational portion 110 defines a hexagonal periphery, but those having ordinary skill in the art will appreciate that the anti-rotational portion 110 could be octagonal or have other polygonal configurations as are well known in the art. The portion 110 may also be replaced with a portion having a substantially circular cross-section and outer periphery.

As shown in FIG. 16, for example, in various exemplary embodiments, the implant engaging post 185 may be received in a corresponding opening 385 in the implant 300, with the abutment 100 being tapped into secure engagement with the implant 300. By way of example, such posts may provide an anti-rotational and secure engagement of the abutment with the implant, for example, by being configured to fit within a tapered opening in the implant, by having a lateral surface that is polygonal in cross-section (e.g., hexagonal or octagonal) and configured to fit within a similarly configured opening in the implant, or a combination thereof. Those ordinarily skilled in the art would be familiar with various types of engagement mechanisms that could be used to secure the abutment to the implant, including, for example various internal or external polygonal and anti-rotational surfaces, tapered surfaces, lobed channels, and/or combinations thereof. Furthermore, although an anti rotational portion 110 is shown in the exemplary embodiment of the abutment 100, those having ordinary skill in the art would understand that various other engagement mechanisms may be utilized in lieu of or in addition to the anti-rotational portions to engage the post 185 of the abutment with a dental implant. In various embodiments, for example, the implant engaging post may comprise screw threading configured to engage with complimentary screw threading on an internal surface of an implant. Thus, as would be understood by those of ordinary skill in the art, depending on the type of engagement mechanism used, the abutment 100 can also have an opening 115 in the coronal end 190 for receiving a screw driver or other tool used to drive the abutment 100 into the implant.

As illustrated in FIG. 2, the abutment 100 defines a substantially tapered (e.g., generally frustro-conical portion) 140 extending from the implant engaging post 185 to a location about mid-way to about ⅔ of the length L of the abutment 100 measured from the apical end 180. The tapered portion 140 of the abutment 100 has a peripheral outer surface that tapers at an angle α in a direction toward the apical end 180. The tapered portion 140 defines a shoulder 130 where the portion 140 meets the post 185.

The tapered portion 140 can be configured to engage with an internal similarly tapered (e.g., generally frustro-conical) interior seat region of an implant. In various exemplary embodiments, the angle, α, of the peripheral surface of the tapered portion 140 is configured to correspond to a tapered internal surface portion of the coronal neck of an implant that receives the abutment 100. Providing such a tapered portion 140 on the abutment, the angle of which may substantially correspond to the taper angle of an internal surface portion at the coronal neck of the implant with which the abutment mates, may provide a substantially flush mating engagement between the abutment and the implant, which may enhance the accuracy of the fit and proper seating of the abutment on the implant. In various exemplary embodiments, the tapered portion 140 can be configured similar to a Morse taper (albeit at a different taper angle), which may render the abutment 100 non-rotational under occlusal (chewing) load once seated in the implant coronal neck portion; in other words, taking more force to loosen (e.g., unscrew) the abutment than to secure it to the implant.

In various exemplary embodiments, the angle α of the taper of peripheral surface of the frustro-conical portion 140 may range from about 1.5° to about 15°, for example, about 5° to about 10°. For example, various implants with which the abutment 100 may be configured to engage may have an internal frustro-conical coronal neck opening having an internal taper angle ranging, for example, from about 1.5° to about 15°. For example, the taper angle may be about 1.5°, about 5.8°, about 8°, about 11° or about 15°, and thus, the angle α may be about 1.5°, about 5.8°, about 8°, about 11°, or about 15°, respectively.

As discussed above, the coronal portion of the abutment 100 can be modified in various ways to achieve a secure, anti- or non-rotational engagement of the abutment with an implant and the features 185, 110, and 140 can be modified as appropriate and as would be understood by those having ordinary skill in the art depending upon the implant with which the abutment is to be engaged. By way of example only, only one of the features 140 or 110 may be provided and/or a feature that combines a tapered portion with a polygonal anti-rotation peripheral surface may be provided. Moreover, although the exemplary embodiment of the abutment 100 shows a tapered portion 140 that is configured to engage with an internal tapered seat region on an implant, those having ordinary skill in the art would understand that various other mating configurations (which define various other shoulder regions, for example, coronal to the implant mating portion of the abutment) may be utilized in lieu of or in addition to the tapered portion 140.

As also depicted in the exemplary embodiment of FIG. 2, the abutment 100 includes a component supporting portion 150, and a gingival cuff 160 that extends between the tapered portion 140 and the component supporting portion 150. The length of the gingival cuff 160 from the tapered portion 140 to the component supporting portion 150 may range from about 1 mm to about 4 mm, for example, and is generally selected depending on the patient. Providing a retention mechanism between the abutment and an implant component (e.g., a coping) as discussed in further detail below may, however, promote the ability to provide a uniform gingival cuff size of about 1 mm, since little or no cement (or other adhesive) is needed to secure the coping to the abutment, which therefore reduces the risks associated with irritating the patient's gingiva.

The gingival cuff 160 may further define a small shoulder 165 positioned at a coronal end thereof where the gingival cuff 160 meets the component supporting portion 150. The shoulder 165 can be formed by the slight diameter change between the gingival cuff 160 and the smaller diameter of the component supportion portion 150. When a component, such as, e.g., a coping, is engaged to the abutment 100, the shoulder 165 can provide a finish line with which an apical end of the component mates. In various exemplary embodiments, for example, the shoulder 165 may be slightly beveled (angled) and various components (e.g., a temporary coping as described in more detail below) may have apical ends providing angled surfaces configured to result in a flush mating contact with the shoulder 165. In various additional embodiments (not shown), the end of the gingival cuff opposite the shoulder may be provided with an angled surface configured to mate in a flush contacting manner with a shoulder on an implant with which the abutment engages.

The component supporting portion 150 extends from approximately mid-length to ⅔ the length L of the abutment 100 from the coronal end 190 to the apical end 180. In various embodiments, for example, the component supporting portion 150 has a length l (see FIG. 2) of about 0.1115 in. The component supporting portion 150 may have a peripheral surface that tapers inwardly toward the coronal end 190. In various exemplary embodiments, the component supporting portion 150 may taper at an angle, β (see FIG. 2), ranging for example, from about 2° to about 12° (e.g., having an included angle ranging from about 4° to about 24°), for example, from about 5.5° to about 6.5°, for example, the angle β may be about 6°.

As shown in FIGS. 1 and 2, the component supporting portion 150 can include a key feature configured to mate with a complimentary key feature on a component to be supported on the abutment. More specifically, in the exemplary embodiment illustrated in FIGS. 1 and 2, the component supporting portion 150 of the abutment 100 includes on an outer surface thereof a flat surface portion 120 and a relief feature, which in the exemplary embodiment shown is a male relief feature 122 that extends along a length (e.g., extends longitudinally) of the flat surface portion 120. As illustrated in the exemplary embodiment of FIGS. 1 and 2, the flat surface portion 120 can extend substantially longitudinally (the longitudinal axis A of the abutment 100 being shown in FIG. 2) from about the coronal end 190 to the shoulder 165 of the gingival cuff 160. The male relief feature 122 can extend along substantially the entire length of the flat surface portion 120 and be disposed substantially centrally between the lateral sides 126 defining the flat surface portion 120.

Figure 4:
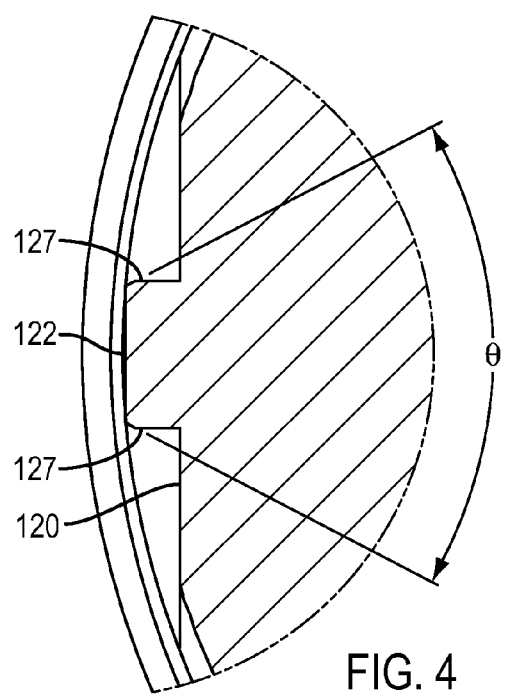
FIG. 4 shows a detailed view of a key feature of FIG. 3.

As best seen in FIGS. 1 and 4, in various exemplary embodiments, the male relief feature 122 is a protrusion that extends radially outward from the flat surface portion 120 of the component supporting portion 150. The protrusion has a substantially rectangular upper surface profile with a thickness that tapers toward the corneal end 190. In various embodiments, for example, the thickness of the protrusion is chosen so that it does not extend (at any point along its length) significantly beyond the remaining outer peripheral surface portions (i.e., the non-flat surface portions) of the component supporting portion 150. In other words, the outer peripheral surface of the protrusion may have the same curvature and taper as the outer peripheral surface of the component supporting portion 150. As shown in FIG. 4, in various exemplary embodiments, the sides 127 (i.e., lateral surfaces) of the protrusion are beveled. In various embodiments, for example, the sides 127 of the protrusion 122 are beveled at an angle, θ, of about 60°.

Figure 3:
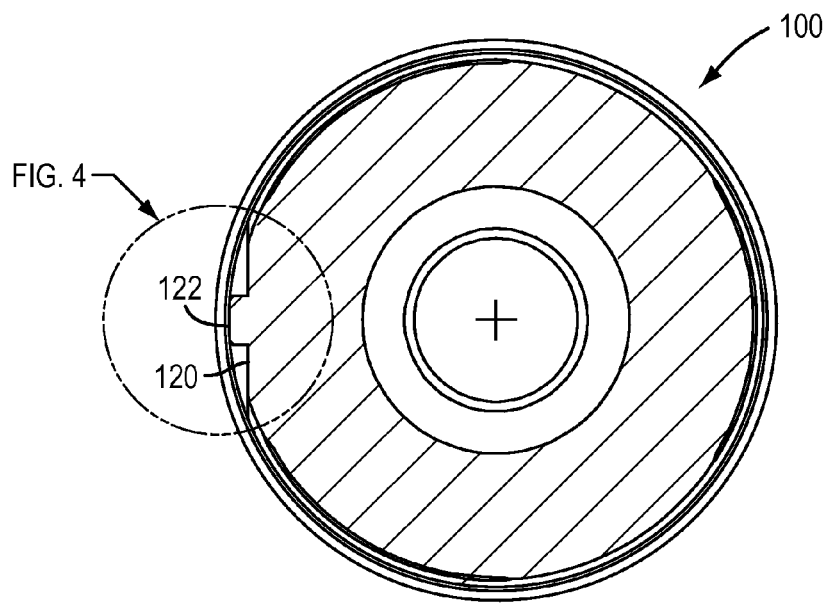
FIG. 3 is a cross-sectional view of the abutment of FIG. 2 taken through line 3-3 of FIG. 2.

Accordingly, the component supporting portion 150 is configured for keyed mating engagement, and provides a key feature that in the exemplary embodiment includes the male relief feature 122 (i.e., a longitudinal protrusion on an outer peripheral surface of the component supporting portion 150) as best seen in FIGS. 3 and 4. The male relief feature 122 is configured, for example, to assist in positioning various components on the component supporting portion 150 (i.e., via a complimentary female relief feature on the respective component), and may further assist in preventing relative rotation between components (e.g., a temporary coping and the abutment 100) during engagement therebetween. Thus, the male and female relief features may act as complimentary key features that provide a keyed mating engagement to prevent rotation between the abutment and the respective component seated thereon. As those of ordinary skill in the art would understand, such components may include but are not limited to, for example, a temporary coping, an impression coping (for use in taking an impression of an implant, e.g., in a patient's mouth), a burnout coping (for use in forming a prosthetic (restoration) from a mold), and/or a framework for a permanent restoration.

Figure 14A:
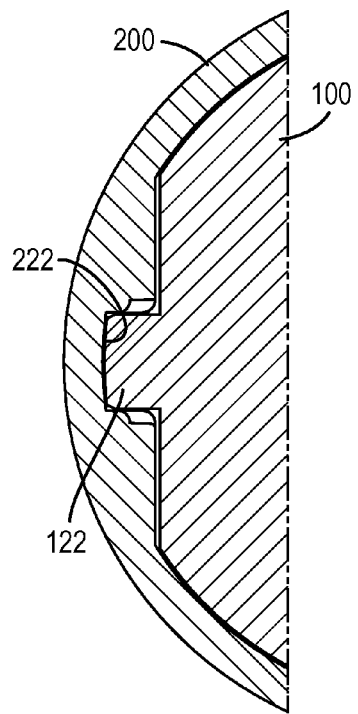
FIGS. 14A-C show partial cross-sectional detailed views of various exemplary embodiments of key features in accordance with the present teachings.

In various exemplary embodiments, the flat surface portion 120 of the abutment 100 may be disposed at a distance ranging from about 0.03 in. to about 0.1 in. from the centerline of the abutment, for example, the distance of the flat surface portion to the centerline of the abutment may be about 0.097 in. Those of ordinary skill in the art would understand, however, that the distance may vary and be selected depending on the size, for example, the diameter of the component supporting portion 150, of the abutment 100. For example, the distance of the flat surface portion 120 to the centerline of the abutment 100 may be about 65% to about 80%, for example, about 72%, of the radius at the corresponding axial location of the component support portion 150. In various additional exemplary embodiments, the male relief feature 122 may have a width of about 0.019 in. Those of ordinary skill in the art would understand, however, that relief features in accordance with the present teachings, may have various dimensions (i.e., lengths, widths, and/or thicknesses), shapes and/or configurations, and that the embodiment of the male relief feature illustrated in FIGS. 1-4 is exemplary only. Thus, although in the exemplary embodiment shown, the male relief feature (protrusion 122) has a substantially rectangular upper surface profile (for keyed mating engagement with a female relief feature with a corresponding substantially rectangular surface profile), as shown in FIG. 14A, those of ordinary skill in the art would further understand that the protrusion may have various other surface profiles, including but not limited to, for example, circular or trapezoidal, as illustrated respectively in FIGS. 14B and 14C.

In various exemplary embodiments, the component supporting portion 150 may also comprise at least one retention feature (e.g., retention groove) around an outer peripheral surface thereof, as disclosed, for example, in U.S. Patent Publication No. 2010/0209877 A1, filed Feb. 13, 2009, the entire contents of which are incorporated by reference herein. As shown in FIGS. 1, 2 and 6A-C, for example, in various exemplary embodiments, the component supporting portion 150 may comprise a plurality of partial retention grooves 125 (three retention grooves 125 being shown in the exemplary embodiment of FIGS. 1, 2, and 6A-C) extending in a direction substantially transverse to the longitudinal axis A of the abutment 100, which are separated from one another by non-grooved portions. The retention grooves 125 may be configured to engage with one or more protrusions on a component to achieve a mechanical retention, e.g., via a snap-fit engagement, of the component on the abutment 100. As above, such components may include but are not limited to, for example, a temporary coping, an impression coping, a burnout coping, and/or a framework for a permanent restoration. In various exemplary embodiments, one or more retention grooves, such as, for example, the retention grooves 125, may be positioned along a length of the portion 150 that is located about midway to two-thirds along a length l (see FIG. 2) of the component supporting portion 150 from the shoulder 165 of the gingival cuff 160. In an exemplary embodiment, a centerline of the retention grooves 125 may be positioned at about 0.0570 in. from the gingival cuff 160. Those of ordinary skill in the art would understand, however, that the centerline of the retention grooves may be positioned at various distances from the gingival cuff without departing from the present teachings and claims.

In various exemplary embodiments, the retention grooves 125 may have a radiused surface profile. The surface of the retention groove 125 may, for example, define a radius of curvature ranging from about 0.010 in. to about 0.060 in. The retention grooves 125 in the exemplary embodiment of FIGS. 1-6, extend around the outer peripheral surface of the abutment 100 at about 60° intervals (i.e., the grooves 125 are equally spaced about every 60°) between the sides 126 of the flat surface portion 120, for example, extending substantially around the entire periphery of the abutment 100 with the exception of the flat portion 120 (see FIGS. 6A-C). Those having ordinary skill in the art would understand, however, that the embodiment shown in FIGS. 1-6 is exemplary only and that the retention grooves 125 may extend around the outer peripheral surface of the abutment 100 at intervals of about 10° or greater between the sides 126 of the flat surface portion 120. In various exemplary embodiments, the grooves 125 may be equally spaced from each other or variably spaced (i.e., having any desired spacing) around the outer peripheral surface of the abutment 100.

In various exemplary embodiments, each retention groove may have a height (measured along the longitudinal axis of the abutment 100) ranging from about 0.015 in. to about 0.040 in., for example, about 0.021 in. In an exemplary embodiment, the retention grooves 125 may be machined to a depth ranging from about 0.001 in. to about 0.004 in., for example, 0.003 in. In various additional embodiments, as best shown in FIGS. 1 and 2, a top edge 175 of each retention groove 125 may blend with the taper of the component supporting portion 150. That is, the top edge 175 of each groove 125 may gradually extend radially outward from within each groove 125 to blend and form a smooth transition with the taper of the component supporting portion 150. In an exemplary embodiment, the top edge 175 of each retention groove 125 may, for example, have a blended radius of about 0.007 in. Those of ordinary skill in the art would understand, however, that the top edge 175 of each groove 125 may have any radius that achieves a blending of the groove 125 with the tapered outer surface of the component supporting portion 150. Such a blended configuration may, for example, prevent damage to corresponding protrusions (e.g., on a temporary coping as described below) when engaging and disengaging the protrusions from the retention grooves 125.

Although the exemplary embodiment of FIGS. 1-6 depicts three retention grooves 125, those having ordinary skill in the art will appreciate that any number of retention grooves may be provided around the outer peripheral surface of the component supporting portion 150, disposed at locations so as to enable one or more protrusions on a coping (or other component) to engage in a snap-fit manner therewith. Moreover, retention grooves in accordance with various exemplary embodiments, rather than extending around all or a portion of the outer peripheral surface, could provide an indented relatively local radiused configuration configured to engage with one or more protrusion features on a coping or other component utilized with dental implant systems to provide a snap-fit engagement to the abutment.

Figure 5:
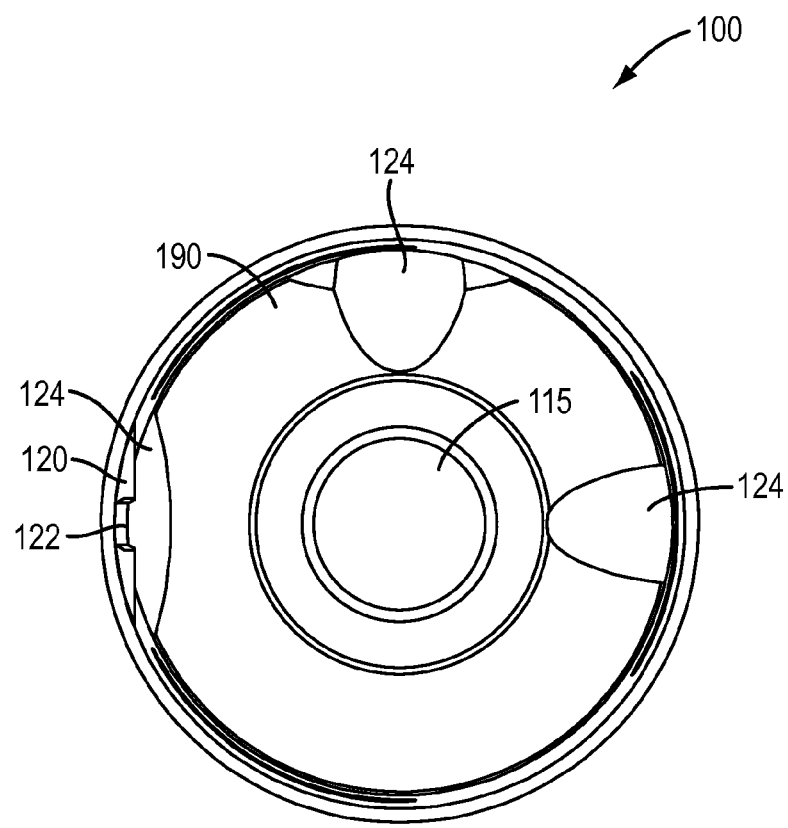
FIG. 5 is a coronal end view of the abutment of FIG. 1.
Figure 6A:
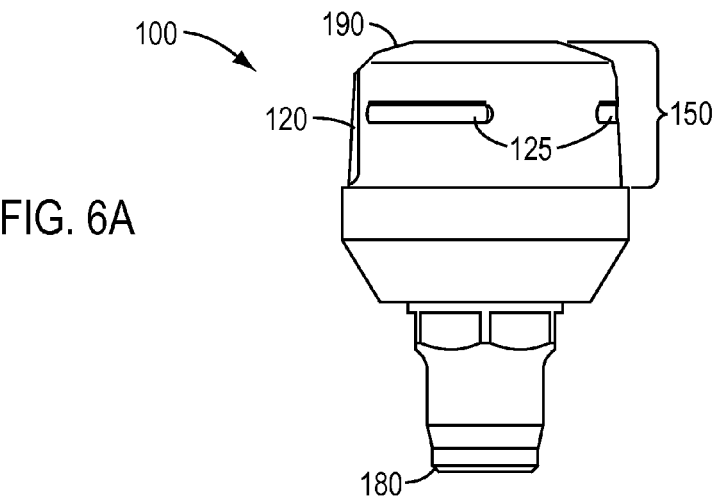
FIGS. 6A-C show additional side views of the abutment of FIG. 1.
Figure 6B:
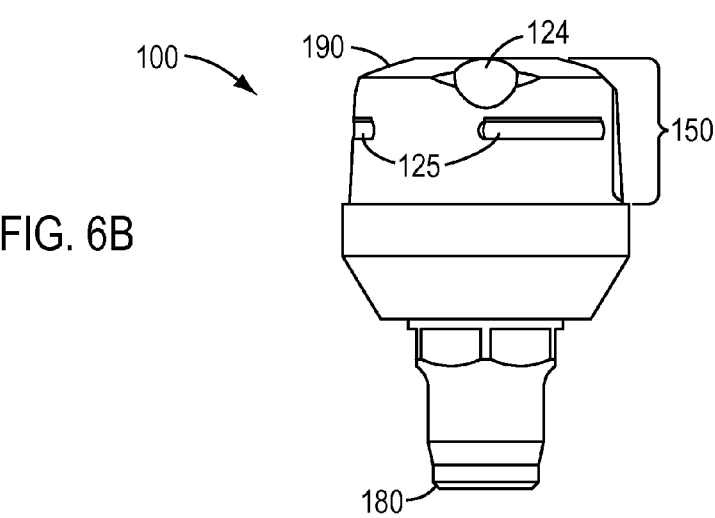
Figure 6C:
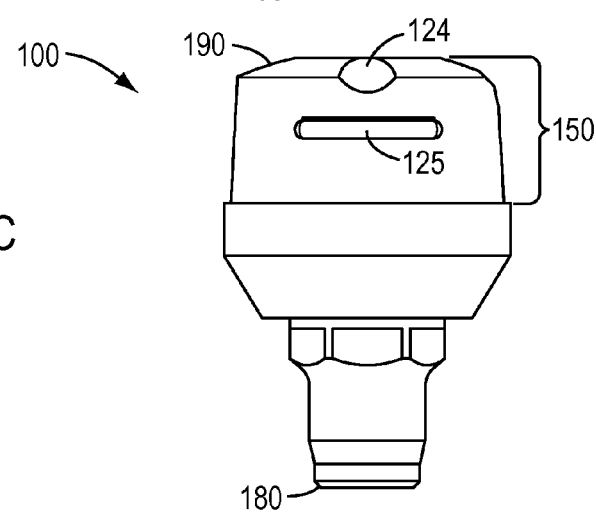

As best seen in FIG. 5, in various exemplary embodiments, the coronal end 190 of the component supporting portion 150 may optionally comprise coding features 124. As those of ordinary skill in the art would understand, the coding features 124 may, for example, be read (e.g., via a scanning device as those having ordinary skill in the art are familiar with) to provide more precise impression taking.

As above, in accordance with various exemplary embodiments, the component supporting portion 150 may have a length l (see FIG. 2) of about 0.1115 in. Those of ordinary skill in the art would understand, however, that the component supporting portion 150 may have various lengths depending on the application of the abutment 100. Likewise, abutments in accordance with various exemplary embodiments of the present teachings may have various diameters. Those having ordinary skill in the art would understand, for example, that the dimensions of abutments and corresponding portions thereof may be modified in accordance with the present teachings in order to fit with various implant configurations, coping configurations, framework configurations, and/or as desired to satisfy a particular patient and/or need; the dimensions set forth herein are non-limiting and exemplary only. For example, those ordinarily skilled in the art would appreciate a variety of abutment dimensions selected so as to mate with a variety of internal, conically-tapered implant configurations, with which those having ordinary skill in the art are readily familiar. Those ordinarily skilled in the art would further appreciate that the total abutment length (TAL) may be selected based upon the coping configuration chosen. In various embodiments, for example, to fit a 4 mm coping the abutment may have a TAL of about 0.323 in. In various additional embodiments, to fit a 6 mm coping the abutment may have a TAL of about 0.402 in. And in various further embodiments, to fit an 8 mm coping the abutment may have a TAL of about 0.481 in. Those of ordinary skill in the art would understand, however, that an abutment in accordance with the present teachings may have various TALs depending upon the coping configuration chosen. In various embodiments, for example, the abutment may have a TAL ranging from about 2 mm to about 9 mm. And in various additional embodiments the abutment may have a TAL ranging from about 4 mm to about 7 mm.

In an exemplary embodiment, the abutment 100 may be machined in order to provide precise tolerances of the various features of the abutment, including, for example, the key feature (e.g., flat surface portion and/or relief feature), the retention features, the tapered portions, etc., so as to ensure an accurate and precise fit with the implant and/or other components configured to be secured to the abutment. In an exemplary embodiment, the abutment may be made from cold-worked, commercially pure, Grade 4 titanium or other medical grade titanium or titanium alloy. However, any biocompatible material providing sufficient strength and durability, such as, for example, a variety of biocompatible titanium materials, may be used to make an abutment in accordance with various exemplary embodiments of the present teachings. Although using a radiopaque material for the abutment may provide sufficient strength, for example to withstand occlusal loads, as well as permitting X-ray observation, other materials also may be suitable, including, for example, composites comprising ceramic and zirconium, composites comprising titanium and zirconium, and other zirconium composites or alloys.

Figure 18:
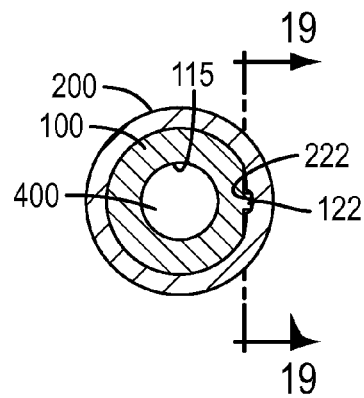
FIG. 18 is a cross-sectional view of the assembly of FIG. 15 taken through line 18-18 of FIG. 15.

As would be understood by those of ordinary skill in the art, abutments in accordance with various exemplary embodiments, such as the exemplary embodiment of FIGS. 1-6, may be configured to be screw-retained in the implant and thus may be configured to receive a retention screw. By way of example, as shown in FIGS. 1 and 5, the abutment 100 may have a channel 115 extending through the length L (see FIG. 2) of the abutment, for receiving a screw to secure the abutment 100 to an implant. As shown in FIGS. 16 and 18, for example, in various embodiments, the abutment 100 may receive a retention screw 400 through a channel 115 to secure the abutment 100 to the implant 300.

Referring now to FIGS. 7-13, an exemplary embodiment of a temporary coping configured to mate with the abutment 100 in accordance with the present teachings is illustrated. As shown in FIGS. 7, 8, 12 and 13, a temporary coping 200 has a substantially cylindrical, hollow configuration having an apical end 280 and a coronal end 290. The temporary coping 200 is configured to be advanced over an abutment, such as abutment 100, as shown, for example, in FIGS. 15-19.

As is perhaps best shown in FIGS. 12 and 13, the interior of the temporary coping 200 presents a tapered surface portion 270 from the apical end 280 toward the coronal end 290, which surface portion 270 terminates below (in the orientation of FIGS. 12 and 13) a coronal end 290 of the coping 200. The degree of taper may substantially correspond to the taper of the component supporting portion of an abutment with which the temporary coping is engaged, such as, for example, component supporting portion 150 of abutment 100. For example, the angle of taper, $\theta$, may range from about 2° to about 12° (e.g., having an included angle ranging from about 4° to about 24°), for example, from about 5.5° to about 6.5°, for example, 8 may be about 6°. As would be understood by those of ordinary skill in the art, the length and other dimensions of the temporary coping 200 may be selected as desired based on the implant and abutment dimensions. In various exemplary embodiments, for example, internal dimensions (such as, for example, the diameter and length of tapered surface portion 270) of the temporary coping 200 may be selected so as to provide a substantially flush mating surface contact (i.e., within machining tolerances) between the internal peripheral surfaces of the temporary coping 200 and the outer peripheral surfaces of the component supporting portion of an abutment (e.g., portion 150 of abutment 100) with which the temporary coping 200 is engaged.

In various additional embodiments, the interior of the temporary coping 200 may further comprise angled surfaces 265 at the apical end 280. In various embodiments, for example, the angled surfaces 265 are configured to result in a flush mating contact with the shoulder 165 (see FIG. 2) of the abutment 100.

In various exemplary embodiments, it may be desirable to provide a temporary coping with an apical end configuration that helps to prevent the risk of potentially cracking the coping as it is placed into engagement with an abutment. For example, such apical end configurations, as described in further detail below, can be desirable when the temporary coping is formed of a relatively brittle (less compliant) material, including but not limited to, for example bis-acrylic and/or bis-acrylic composite dental restoration materials. In various exemplary embodiments, for example, the apical end of a coping may have various mating surface features configured to result in a flush mating contact with the shoulder of an abutment having a complimentary mating surface feature. This can assist in both sealing the area at the interface of the temporary coping and the abutment shoulder (e.g., to prevent infection) and limiting the expansion of the apical end during engagement with the abutment (e.g., to prevent cracking).

Figure 20:
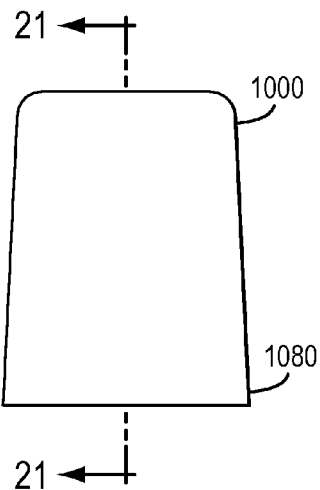
FIG. 20 is a side view of another exemplary embodiment of a temporary coping in accordance with the present teachings.
Figure 21:
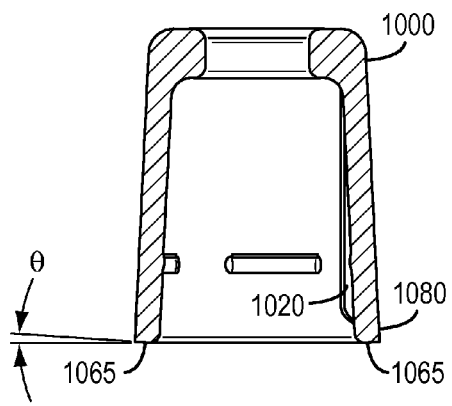
FIG. 21 is a cross-sectional view of the temporary coping of FIG. 20 taken through line 21-21 of FIG. 20.
Figure 22:
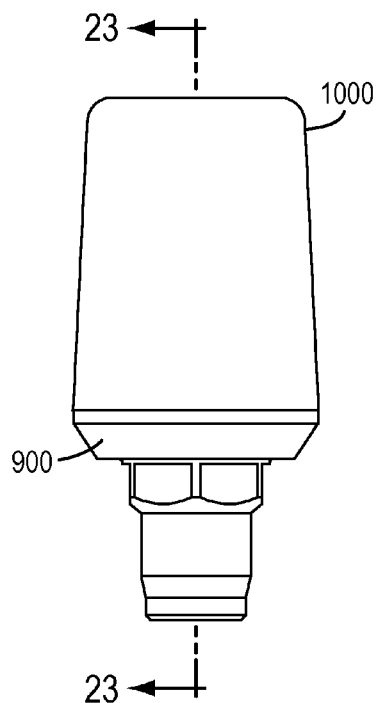
FIG. 22 is a side view of the temporary coping of FIG. 20 engaged with an abutment in accordance with an exemplary embodiment.

As shown in FIGS. 20 and 21, for example, in various exemplary embodiments of the present teachings, a temporary coping 1000 may comprise angled end surfaces 1065 at an apical end 1080 of the coping 1000. In various embodiments, for example, the surfaces 1065 may be angled at an angle θ ranging from about 1° to about 45°. As shown with respect to FIGS. 22, 23, 24A and 24B, the coping 1000 is configured to mate with an abutment 900, such that the angled surfaces 1065 are in a flush mating contact with complimentary angled surfaces 965 of a shoulder 985 of the abutment 900.

Figure 25:
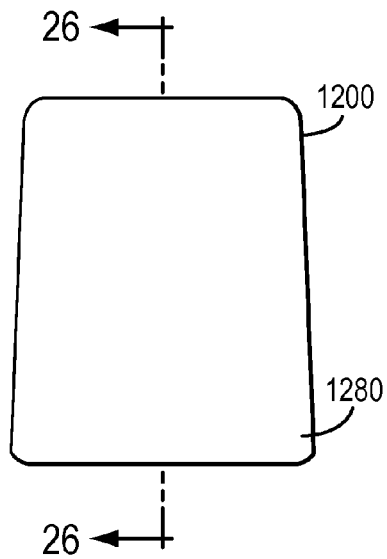
FIG. 25 is a side view of another exemplary embodiment of a temporary coping in accordance with the present teachings.
Figure 26:
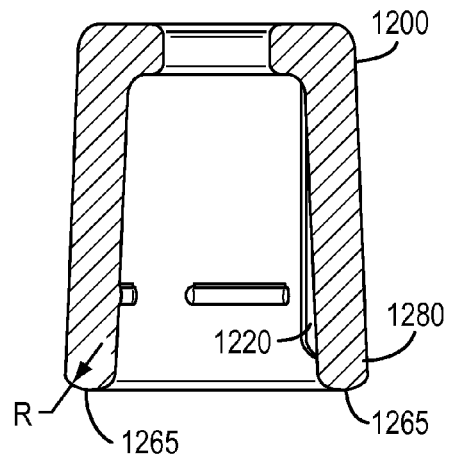
FIG. 26 is a cross-sectional view of the temporary coping of FIG. 25 taken through line 26-26 of FIG. 25.
Figure 27:
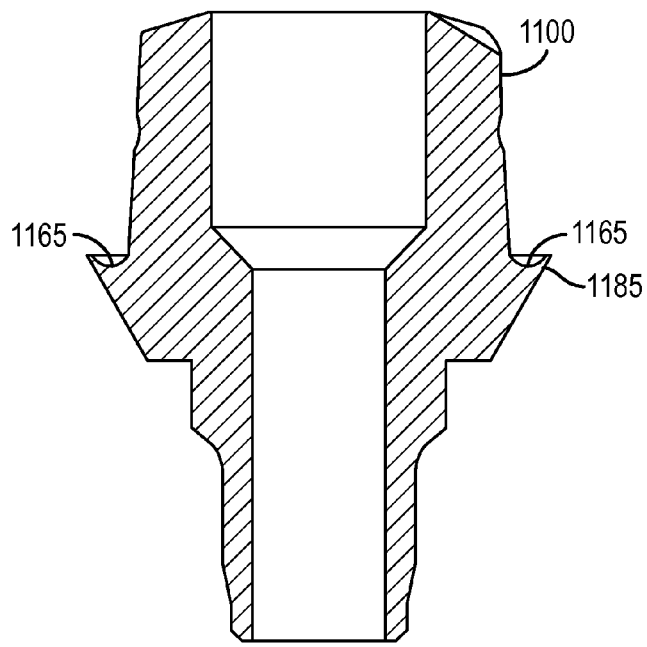
FIG. 27 is a partial cross-sectional view of an exemplary embodiment of an abutment configured to engage with the temporary coping of FIG. 25 in accordance with the present teachings.

In various additional exemplary embodiments, as shown with respect to FIGS. 25 and 26, a temporary coping 1200 may comprise convex end surfaces 1265 at an apical end 1280 of the coping 1200. In various embodiments, for example, the surfaces 1265 may have a radius R that is greater than or equal to about half the thickness of the walls of the coping 1200. Although not shown, as above, the coping 1200 is configured to mate with an abutment 1100 (see FIG. 27), such that the convex surfaces 1265 are in a flush mating contact with complimentary convex surfaces 1165 of a shoulder 1185 of the abutment 1100.

Figure 28:
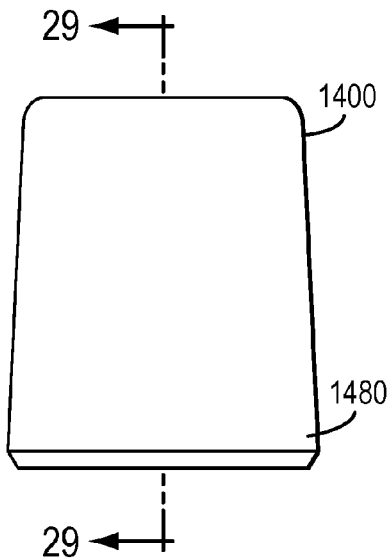
FIG. 28 is a side view of another exemplary embodiment of a temporary coping in accordance with the present teachings.
Figure 29:
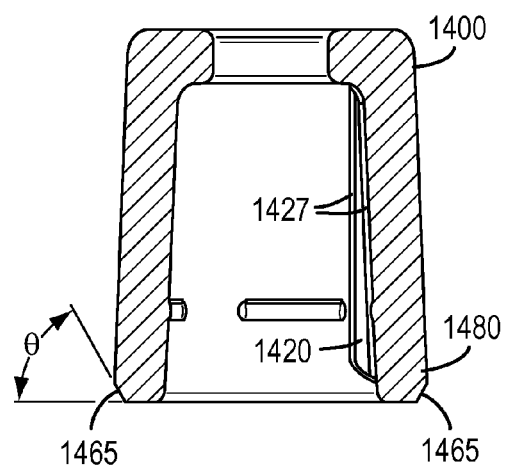
FIG. 29 is a cross-sectional view of the temporary coping of FIG. 28 taken through line 29-29 of FIG. 28.
Figure 30:
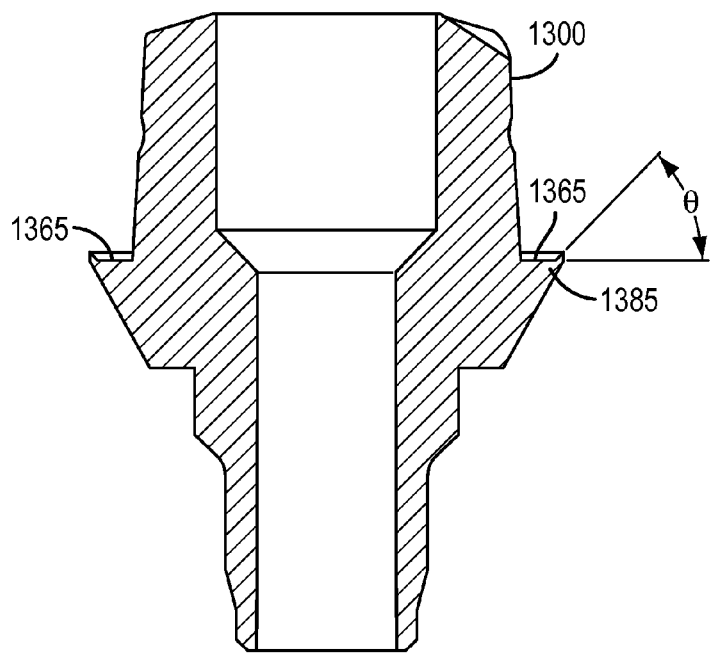
FIG. 30 is a partial cross-sectional view of an exemplary embodiment of an abutment configured to engage with the temporary coping of FIG. 28 in accordance with the present teachings.

In various further embodiments, as shown with respect to FIGS. 28 and 29, a temporary coping 1400 may comprise angled edges 1465 at an apical end 1480 of the coping 1400. In various embodiments, for example, the edges 1465 may be angled at an angle θ ranging from about 15° to about 60°. Although not shown, as above, the coping 1400 is configured to mate with an abutment 1300 (see FIG. 30), such that the angled edges 1465 are in a flush mating contact with complimentary angled edges 1365 of a shoulder 1385 of the abutment 1300.

Figure 31:
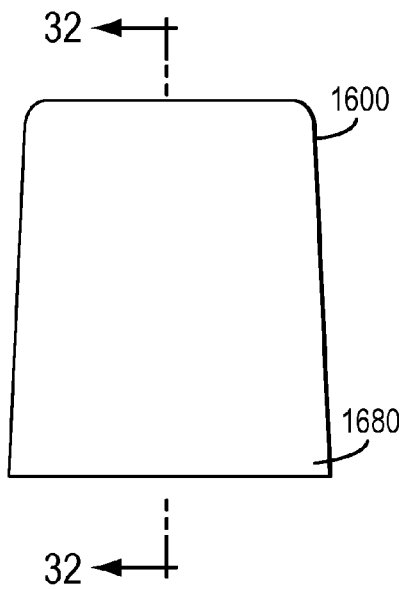
FIG. 31 is a side view of another exemplary embodiment of a temporary coping in accordance with the present teachings.
Figure 32:
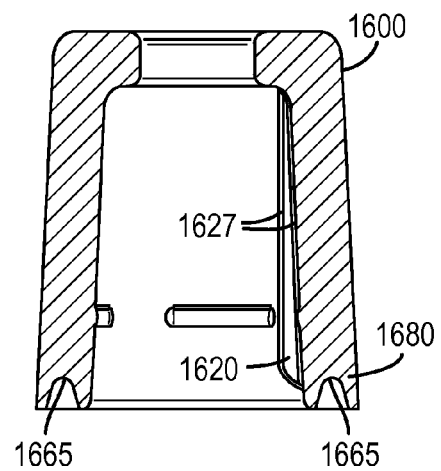
FIG. 32 is a cross-sectional view of the temporary coping of FIG. 31 taken through line 32-32 of FIG. 31.
Figure 33:
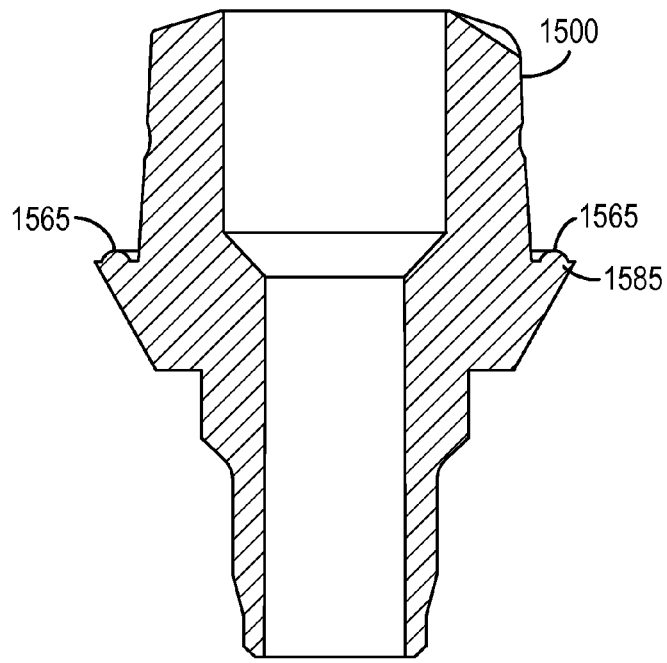
FIG. 33 is a partial cross-sectional view of an exemplary embodiment of an abutment configured to engage with the temporary coping of FIG. 31 in accordance with the present teachings.

As shown with respect to FIGS. 31 and 32, in various additional embodiments of the present teachings, a temporary coping 1600 may comprise a groove 1665 within an apical end surface of the apical end 1680 of the coping 1600. Although not shown, as above, the coping 1600 is configured to mate with an abutment 1500 (see FIG. 33), such that the groove 1665 is in a flush mating contact with a complimentary protrusion 1565 on a shoulder 1585 of the abutment 1500.

Those of ordinary skill in the art will understand that the embodiments depicted in FIGS. 20-33 are exemplary only, and that the present teachings contemplate various configurations of mating features to assist in preventing a temporary coping from cracking as it is expanded into engagement with an abutment without departing from the scope of the present teachings and claims.

Figure 10:
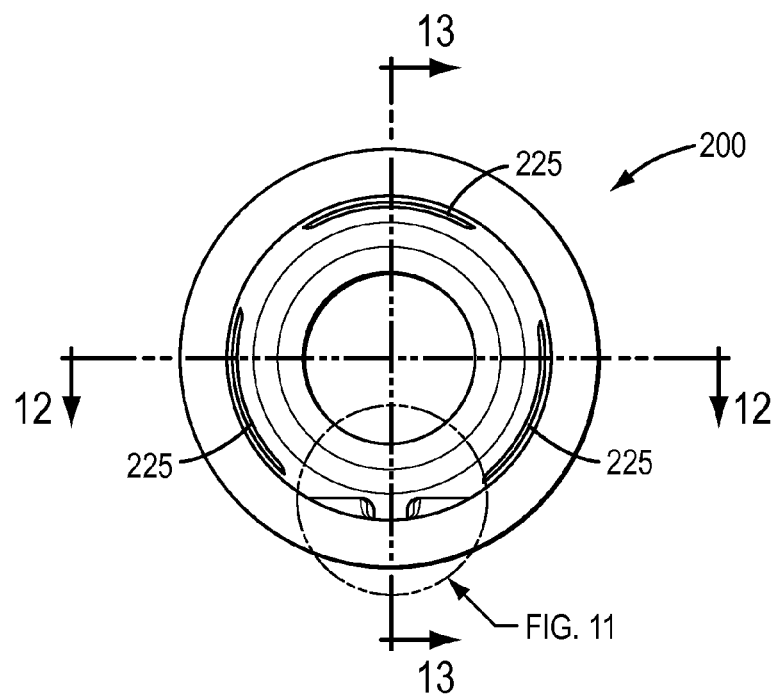
FIG. 10 is an apical end view of the temporary coping of FIG. 7.
Figure 11:
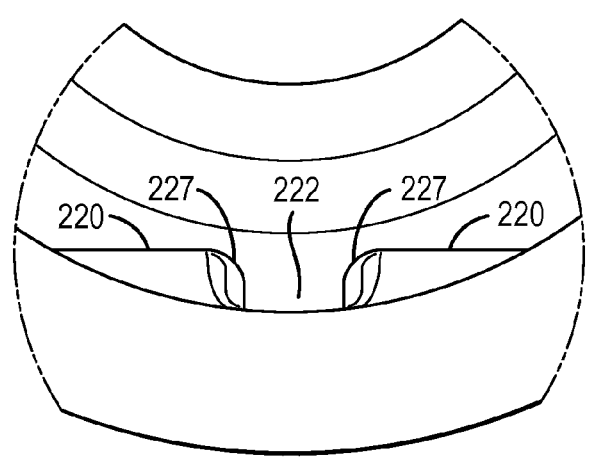
FIG. 11 shows a detailed view of the key feature of FIG. 10.
Figure 19:
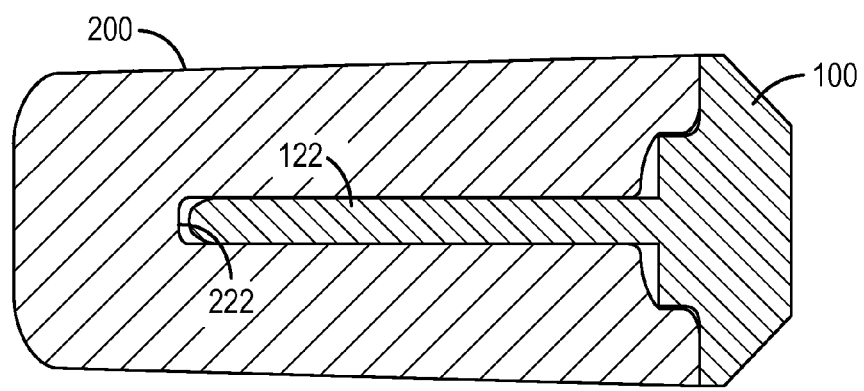
FIG. 19 is a cross-sectional view of the assembly of FIG. 18 taken through line 19-19 of FIG. 18.

As shown in FIGS. 9-13, an internal surface portion of the temporary coping 200 may include a key feature configured to provide a keyed mating engagement with a key feature on an abutment, like abutment 100. For example, in the exemplary embodiment shown, an internal surface of the temporary coping 200 can include two internal flat surface portions 220 of the temporary coping 200 that are raised (i.e., extend radially inwardly) relative to the remaining internal surface portions of the temporary coping 200. The flat surface portions 220 can have opposing edges 227 that are spaced apart and face each other so as to define a slot or groove (i.e., female relief feature) 222 therebetween (see FIG. 12 for example). In other words, the temporary coping 200 may comprise two protrusions (which define the female relief feature) disposed substantially opposite one another to form the longitudinal slot 222 on an inner peripheral surface of the temporary coping 200 as best seen in FIGS. 10 and 11. Thus, the female relief feature may face toward a center of the temporary coping 200, and may be configured for a keyed mating engagement with a male relief feature on the abutment. In other words, the female relief feature may be configured to correspond and receive in a contacting, mating manner (i.e., a substantially flush manner) a male relief feature on the abutment, for example, as shown in FIGS. 14A and 19, the female relief feature 222 may be configured to mate with the male relief feature 122 on abutment 100, to prevent relative rotation of the temporary coping 200 relative to the abutment and/or to assist in orientation of the temporary coping 200 relative to the abutment.

As would be understood by those of ordinary skill in the art, for example, in various embodiments, to prevent rotation between the components, a keyed mating engagement may be achieved between the abutment 100 and the coping 200, through a flush, contacting engagement between the lateral surfaces 127 of the protrusion 122 (see FIG. 4) and the edges 227 of the flat surface portions 220 (see FIG. 11).

As above, those of ordinary skill in the art would understand that relief features in accordance with the present teachings, may have various dimensions (i.e., lengths, widths, and/or thicknesses), shapes and/or configurations, and that the embodiment of the female relief feature illustrated in FIGS. 7-13 is exemplary only. Thus, although in the exemplary embodiment shown in FIG. 14A, the female relief feature (slot 222) has a substantially rectangular surface profile (for keyed mating engagement with the male relief feature 122), those of ordinary skill in the art would understand that the slot may have various surface profiles. In various embodiments of the present teachings, for example, a coping 600 may include a rounded female relief feature 622 configured to mate with a rounded male relief feature 522 on an abutment 500 as illustrated in FIG. 14B. In various additional embodiments, a coping 800 may include a trapezoidal female relief feature 822 configured to mate with a trapezoidal male relief feature 722 on an abutment 700 as illustrated in FIG. 14C.

In various further embodiments of the present teachings, it may be desirable to provide a temporary coping with a larger and/or more substantial key feature that helps to prevent the risk of potentially damaging the key feature as it is placed into engagement with a complementary key feature on an abutment. For example, such key features, as described in further detail below, can be desirable when the temporary coping is formed of a relatively brittle (less compliant) material, including but not limited to, for example, bis-acrylic and/or bis-acrylic composite dental restoration materials.

Figure 23:
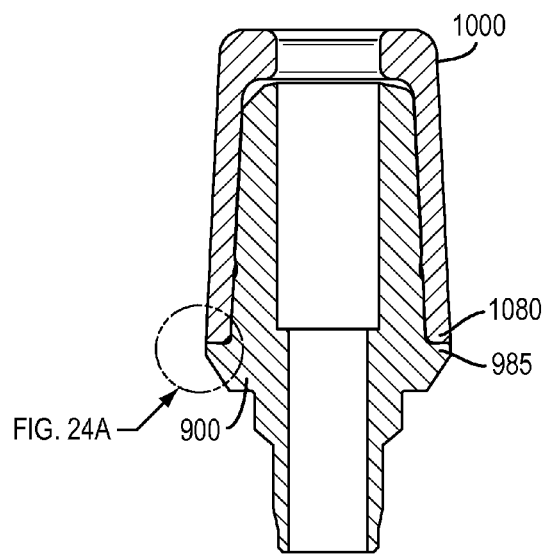
FIG. 23 is a cross-sectional view of the assembly of FIG. 22 taken through line 23-23 of FIG. 22.
Figure 24A:
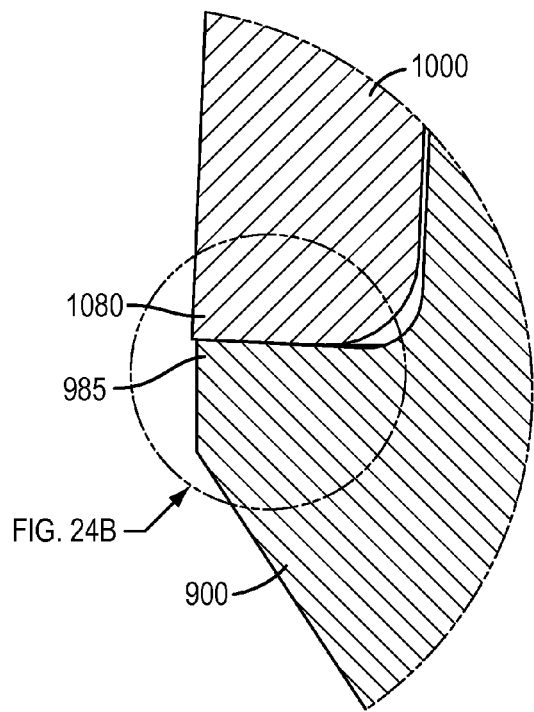
FIGS. 24A and 24B show detailed views of mating interfaces of the temporary coping and the abutment of FIG. 22.
Figure 24B:
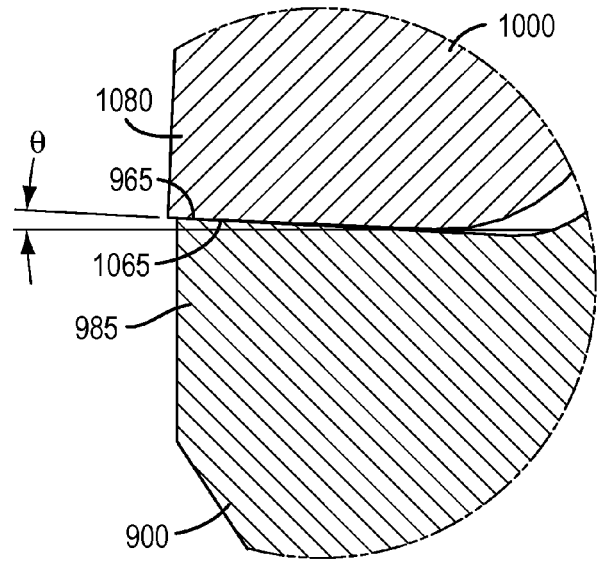

In various exemplary embodiments, as shown with respect to FIGS. 21 and 26, an internal surface of a temporary coping 1000, 1200 can include two internal flat surface portions 1020, 1220 respectively that are raised (i.e., extend radially inwardly) relative to the remaining internal surface portions of the temporary coping, and which extend substantially the entire length of the internal surface of the respective temporary coping 1000, 1200. As shown in FIG. 23 with respect to temporary coping 1000, for example, as above, each coping 1000, 1200 is configured to mate with a respective abutment 900, 1100 (see FIG. 27), such that the internal flat surface portions 1020, 1220 (which define the female relief feature) are configured for a keyed mating engagement with a corresponding male relief feature (not shown) on the abutment.

In various additional exemplary embodiments, as shown with respect to FIGS. 29 and 32, an internal surface of a temporary coping 1400, 1600 can include two internal flat surface portions 1420, 1620 respectively that are raised (i.e., extend radially inwardly) relative to the remaining internal surface portions of the temporary coping. The flat surface portions 1420, 1620 can have fillets 1427, 1627 respectively that wrap around the perimeter of each internal flat surface portion 1420, 1620, such that each internal flat surface portion 1420, 1620 has a blended radius with the remaining tapered inner surface of the coping. Although not shown, as above, each coping 1400, 1600 is configured to mate with a respective abutment 1300, 1500 (see FIGS. 30 and 33), such that the internal flat surface portions 1420, 1620 (which define the female relief feature) are configured for a keyed mating engagement with a corresponding male relief feature (not shown) on the abutment.

Figure 12:
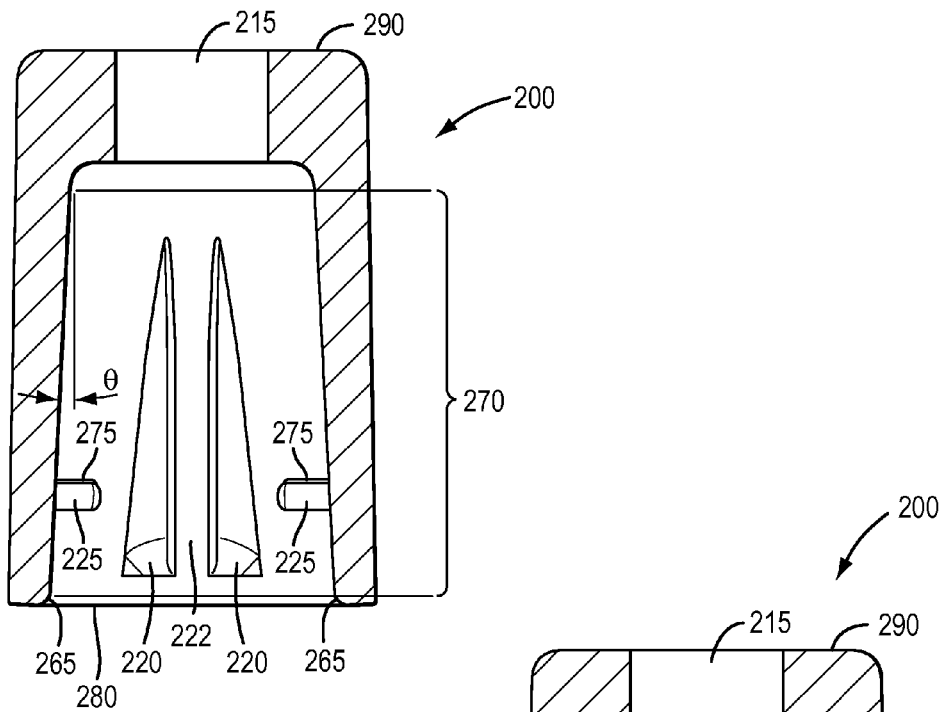
FIG. 12 is a cross-sectional view taken of the temporary coping of FIG. 7 taken through line 12-12 of FIG. 10.
Figure 13:
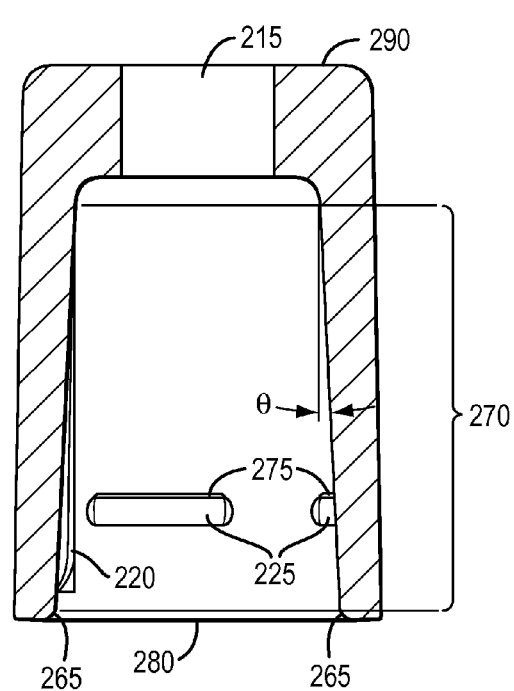
FIG. 13 is a cross-sectional view of the temporary coping of FIG. 7 taken through line 13-13 of FIG. 10.
Figure 14B:
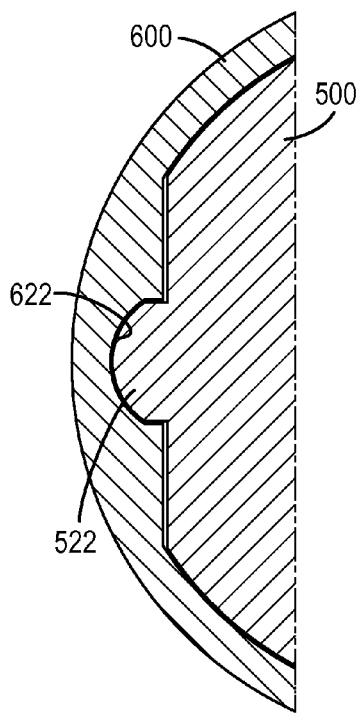
Figure 14C:
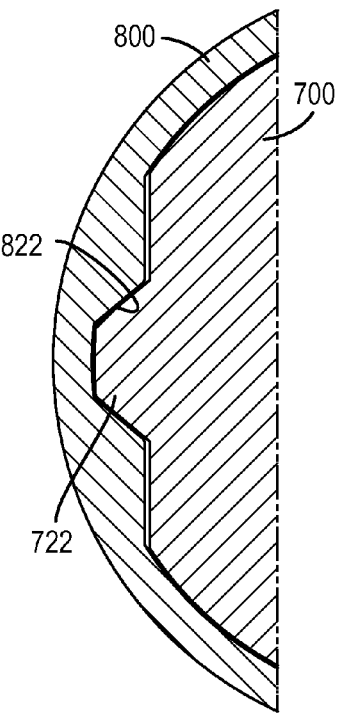

As seen best in FIGS. 10, 12 and 13, provided on the internal peripheral surface of the temporary coping 200 proximate the apical end 280 are retention features to provide a complimentary engagement with the retention features on the abutment 100. As illustrated, in the exemplary embodiment of the temporary coping 200, the complimentary retention features are in the form of protrusions 225 (three protrusions 225 being shown in the embodiment of FIGS. 7-13) that extend, in the exemplary embodiment of FIGS. 7-13, generally transversely around the inner peripheral surface of the coping 200 up to the raised surface portion 220. As shown in FIG. 10, the protrusions 225 are spaced from each other, and are disposed at substantially the same axial location along the internal peripheral surface of the coping 200. Thus, the protrusions 225 can be configured to provide a mating engagement with the retention features (e.g., retention grooves) provided on an abutment, such as, for example, the retention grooves 125 on the abutment 100. The protrusions 225 may, for example, have a convex profile and be configured to engage (e.g., in a snap-fit manner) with retention grooves, e.g., retention grooves 125, on an abutment so as to form an accurate and secure retention of the temporary coping 200 on the abutment. In other words, the protrusions 225 may be configured to mate in a precise and flush manner with the retention grooves 125 when the temporary coping 200 is advanced down over and into mating engagement (e.g., snap-fit) with the abutment 100 as illustrated, for example, in FIG. 17.

In various exemplary embodiments, to prevent the protrusions 225 from being damaged (e.g., being sheared from the inner peripheral surface of coping 200) when the coping 200 is removed from a mold, and/or when the coping is engaged or disengaged from the abutment 100, a top edge 275 (see FIGS. 12 and 13) of each protrusion 225 may be blended with the tapered inner surface portion 270. That is, the top edge 275 of each protrusion 225 may gradually extend radially outward to blend and form a smooth transition with the taper of the surface portion 270. In an exemplary embodiment, the top edge 275 of each protrusion 225 may, for example, have a blended radius of about 0.007 in. Those of ordinary skill in the art would understand, however, that the top edge 275 of each protrusion 225 may have any radius that achieves a blending of the protrusion 225 with the tapered surface portion 270.

Although the exemplary embodiment of FIGS. 7-13 shows a temporary coping provided with three transversely oriented protrusions, those of ordinary skill in the art would understand that various configurations of protrusions may be used to mechanically secure the components (e.g., the temporary coping 200 and abutment 100). As discussed, for example, in U.S. Patent Publication No. 2010/0209877 A1, the entire contents of which are incorporated by reference herein, in various embodiments, a temporary coping may have a single continuous protrusion ring, which extends approximately 270° around an inner peripheral surface of the coping between the opposite sides of the flat surface portion. And in various additional embodiments, a temporary coping may be provided with one or more relatively localized protrusions configured to engage, e.g., in a snap-fit manner, with one or more retention grooves on an abutment in accordance with the present teachings. Those having ordinary skill in the art would recognize various modifications to the protrusions that could be made without departing from the scope of the present teachings.

Furthermore, the configuration (e.g., size and shape) of the protrusions, whether in the form of multiple protrusions, a continuous protrusion ring or one or more relatively localized protrusions, may be chosen based on various considerations, such as, for example, the shape and size of one or more retention grooves with which the protrusions are designed to engage, the desired force required to achieve a mating engagement, e.g., snap-fit engagement, between the protrusions and the retention grooves, and/or the retention force desired between the abutment and temporary coping (e.g., the force needed to disengage the components from one another). Likewise, the number and positioning of the protrusions may vary and may be selected based on similar considerations; the number of protrusions on the temporary coping may range from one to more than one.

By way of example, the one or more protrusions on a temporary coping in accordance with various exemplary embodiments may be configured so as to provide substantially a 100% interference mating fit with one or more corresponding retention grooves on an abutment with which the one or more protrusions are desired to engage. By way of further example, the one or more protrusions on a temporary coping may be configured so as to provide a force ranging from about 2 lb. to about 7 lb. to achieve a mating engagement, for example, via a snap-fit, with one or more retention grooves. In addition, the one or more protrusions on a temporary coping may be configured so as to provide a force ranging from about 2 lb. to about 20 lb. to disengage the protrusions from one or more retention grooves on an abutment (i.e., pull off the temporary coping from the abutment). In the exemplary embodiment of FIGS. 7-13 (with three protrusions 225), for example, the protrusions 225 are configured so as to provide a force of about 2 lb. to disengage the protrusions from the retention grooves 125. Protrusions in accordance with the present teachings are discussed further in U.S. Patent Publication No. 2010/0209877 A1.

As above, abutments in accordance with various exemplary embodiments, such as the exemplary embodiment of FIGS. 1-6, may be configured to be screw-retained in the implant and thus may be configured to receive a retention screw. As shown in FIGS. 16 and 18, for example, the abutment 100 may be retained in the implant 300 via a retention screw 400. Thus, by way of example, as shown in FIGS. 12, 13, and 16, the temporary coping 200 may have a screw access channel 215 in the coronal end 290, for receiving/accessing the screw (e.g., screw 400), which secures the abutment (e.g., abutment 100) to an implant (e.g., implant 300). Those of ordinary skill in the art would understand, for example, that with such a configuration the abutment may be placed and secured within a patient's mouth with the temporary coping already attached to the abutment.

In various exemplary embodiments, temporary copings in accordance with the present teachings may be made of a plastic material that relatively easily permits mating engagement (e.g., via snap-fit engagement) of one or more protrusion features with one or more retention grooves on an abutment. Examples of suitable materials include, but are not limited to, materials comprising poly-ether-ether ketone (PEEK), hybrid PEEK, PEEK polymer, nylon, and/or Delrin. Alternatively, temporary copings in accordance with the present teachings may be made of a metal material, such as, for example, various grades of titanium and titanium alloys. Yet another suitable material for temporary copings in accordance with the present teachings may include a hybrid composite material comprising both metal and plastic.

Various exemplary materials, such as, for example, a bis-acrylic dental restoration material, including a bis-acrylic composite (also known as a bis-acrylic hybrid) material, that permit a chemical bonding of the temporary coping with a temporary replacement tooth veneering material also may be used to form temporary copings in accordance with exemplary embodiments of the present teachings. Such chemical bonding may be used without the need for another bonding mechanism to bond the temporary coping to the temporary replacement tooth veneering material (e.g., acrylic material and/or other material suitable for forming a temporary restoration with which those having ordinary skill in the art have familiarity), although additional bonding mechanisms may be employed. For various materials that may be used to make a temporary coping that achieves such a chemical bonding with the temporary restoration, reference is made to U.S. Patent Publication No. 2010/0151420 A1, filed Dec. 11, 2008, which is incorporated by reference herein in its entirety. One example of a suitable bis-acrylic material that may be used to form a temporary coping in accordance with various exemplary embodiments includes Protemp™ Plus Temporization Material available by 3M ESPE. Other nonlimiting examples of suitable bis-acrylic composites that may be used to form a temporary coping according to the present teachings may include, but are not limited to, for example, Luxatemp®, a composite of bis-acrylic, glass powder, and silica, available from DMG; InstaTemp® Max, a composite of bis-acrylic, glass powder, and silica, available from Sterngold Dental; Structur Premium, Acytemp, Integrity Fluorescence, and Kanitemp Royal.

Although the exemplary embodiments of FIGS. 1-14A and 15-19 described and shown herein show an abutment 100 including a key feature comprising a male relief feature (e.g., a flat surface portion and longitudinal protrusion) and a temporary coping 200 including an key feature comprising a female relief feature (e.g., a flat surface portion and longitudinal slot), those of ordinary skill in the art would understand that the key feature of the abutment 100 could include a female relief feature configured for keyed mating engagement with a male relief feature on the temporary coping 200. Thus, although not shown, various exemplary embodiments of the present teachings further contemplate an abutment comprising a component supporting portion having a female relief feature (e.g., a slot extending longitudinally from a top portion of a flat surface to a bottom portion of the flat surface). And a temporary coping configured to receive the component supporting portion and comprising a male relief feature (e.g., a longitudinal protrusion) configured for keyed mating engagement with the longitudinal slot in the abutment. Further, as mentioned above, the abutment and component (e.g., coping) to be engaged with the abutment can each include a combination of male and/or female relief features complimentary to each other to provide a keyed mating engagement of the abutment with the component.

Moreover, although the exemplary embodiments of FIGS. 1-14A and 15-19 described and shown herein show an abutment 100 including retention grooves around an outer surface thereof, and a temporary coping 200 including protrusions around an inner surface thereof, those of ordinary skill in the art would understand that the abutment 100 could include protrusions configured for snap-fit engagement with grooves on the temporary coping 200. Thus, although not shown, various exemplary embodiments of the present teachings further contemplate an abutment comprising one or more protrusions to provide snap-fit engagement with corresponding grooves on a temporary coping.

Also, although various exemplary embodiments of the present teachings described herein utilize a snap-fit engagement between one or more protrusions and one or more grooves to provide axial retention, it is envisioned that the mating engagement between such protrusions and retention grooves may include various interference fits sufficient to achieve the desired retention of a component on an abutment. Thus, it should be understood by those ordinarily skilled in the art that the retaining mating engagement between protrusions and retention grooves in accordance with various exemplary embodiments of the present teachings may not necessarily result in an audible and/or tactile "snap" when engagement of those parts occurs.

Various exemplary embodiments of the present teachings additionally contemplate a method for orienting a component, such as, for example, a coping, within a patient's body. In various embodiments, for example, a coping, such as, for example, a temporary coping 200 may be advanced substantially in an axial direction over an abutment, such as, for example, an abutment 100. To precisely orient the coping 200 on the abutment 100, the coping 200 may be rotated, for example, until the key feature on the coping 200 is directly over a corresponding key feature on the abutment 100. Thus, in the exemplary embodiments herein, the coping 200 is oriented relative to the abutment 100 so that the slot 222 receives the protrusion 122 and the respective flat surface portions 220 and 120 align and mate with each other. In this orientation, the coping 200 can then be advanced in the axial direction downwardly onto the abutment 100 (see FIGS. 16 and 19). The coping 200 can be advanced, for example, with a force sufficient to achieve a mating engagement between the retention grooves 125 on the abutment 100 and the protrusions 225 on the coping, for example, via a snap-fit. By way of example, to achieve a snap-fit engagement, the coping 200 can be advanced with a force ranging from about 2 lb. to about 7 lb. Accordingly, the keyed mating engagement via the respective key features (e.g., 120, 122, 220, 222) of the abutment 100 and the coping 200 can prevent relative rotation between those parts and the engagement of the retention grooves 125 and the protrusions 225 can prevent axial movement between those parts (at least when a pull-off force is under a predetermined, threshold level).

Although various exemplary embodiments of the abutments described herein have been described as configured to be used with temporary copings, it is envisioned that abutments in accordance with the present teachings may be configured for use with various components, including, for example, impression copings, burnout copings, and/or a framework for a permanent restoration to name a few.

Moreover, in order to construct a permanent restoration, as would be understood by those of ordinary skill in the art, various exemplary embodiments of the present teachings also contemplate the use of an analog having substantially the same coronal portion configuration (e.g., component supporting portion) as that of exemplary embodiments of abutments of the present teachings. For example, with reference to the abutment 100 of the exemplary embodiment of FIGS. 1-6, an exemplary embodiment of the analog in accordance with the present teachings presents a configuration having the same configuration as, for example, the component supporting portion 150.

Furthermore, although various exemplary embodiments described herein have been described as configured to be used with dental implants, it is envisioned that the various components in accordance with the present teachings may be configured for use with other types of bone and/or cartilage implants, including, for example, extra-oral and/or orthopedic implants, for which it may be desirable to take an impression. Examples of extra-oral implants may include, for example, implants used for prosthetic eyes, ears, or noses.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the written description and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the devices and methods of the present disclosure without departing from the scope of its teachings. By way of example, various dimensions, shapes, materials, and/or arrangements of parts may be altered based on desirable features and/or applications, and those having ordinary skill in the art would recognize how to make such modifications in light of the present teachings. By way of example, although in the exemplary embodiments shown and described above, the protrusions had generally radial profiles (e.g., semi-spherical), those having ordinary skill in the art that would understand that various shapes and configurations of protrusions for engaging with retention grooves, including but not limited to, for example, rectangular, cubical, pyramidal, etc. may be used without departing from the scope of the present teachings. In addition, although in the exemplary embodiments above, various retention grooves are shown and described as radiused grooves having a substantially arc-shaped profile, those having ordinary skill in the art would understand that such grooves could have a variety of shapes, including, but not limited to, for example, notch-shaped (e.g., V-shaped), or presenting multiple sides.

Furthermore, although in the exemplary embodiments shown and described above, the key features (e.g., protrusions and slots) had generally rectangular profiles, those having ordinary skill in the art would understand that various shapes and configurations of male and female key features (i.e., keys and keyways), including but not limited to, for example, circular, cubical, pyramidal, trapezoidal, etc. may be used without departing from the scope of the present teachings. In addition, although in the exemplary embodiments above, various key features are shown and described as having flat surface portions, those having ordinary skill in the art would understand that such surface portions could have a variety of configurations and shapes, including, but not limited to, for example, ridged and/or convex/concave surfaces.

In the exemplary embodiments described above, various features have been discussed. Those having ordinary skill in the art would recognize that in some cases, features described with respect to one exemplary embodiment may be combined and/or used in conjunction with another exemplary embodiment even if not specifically described herein. The present teachings are intended to cover such modifications and combinations as would be apparent to those ordinarily skilled in the art.

The various exemplary embodiments described and shown herein are not intended to limit the present teachings. To the contrary, the present teachings are intended to cover alternatives, modifications, and equivalents. Other embodiments of the present teachings will be apparent to those skilled in the art from consideration of the specification and practice of the present teachings disclosed herein. It is intended that the specification and exemplary embodiments be considered as exemplary only, with the claims being provided a scope of a breadth supported by the present teachings.

What is claimed is:

1. A system for securing a coping within a patient's body, the system comprising:
   an abutment comprising:
      an implant engaging portion configured to engage with a dental implant,
      a component supporting portion having a key feature on an external surface portion,
      a tapered portion extending in a coronal direction from the implant engaging portion, and
      a gingival cuff extending between the tapered portion and the component supporting portion, wherein the gingival cuff defines a shoulder at a coronal end, the shoulder being disposed where the gingival cuff meets the component supporting portion; and
   a coping having a complimentary key feature on an internal surface portion,
   wherein the key feature of the abutment comprises, on an outer peripheral surface of the component supporting portion, a flat surface portion and an elongate male relief feature extending along the flat surface portion in a direction of a longitudinal axis of the abutment,
   wherein the complimentary key feature of the coping comprises, on an inner peripheral surface thereof, a flat surface portion and an elongate female relief feature extending along the flat surface portion in a direction of a longitudinal axis of the coping,
   wherein the key feature and the complimentary key feature are configured to provide a keyed mating engagement of the coping and the abutment, and
   wherein an apical end surface of the coping and the shoulder of the gingival cuff are configured to be flushly mated with each other when the coping and the abutment are in keyed mating engagement.

2. The system of claim 1, wherein the coping is a temporary coping.

3. The system of claim 2, wherein the temporary coping is made from a material that permits chemical boding of the temporary coping with a veneering material of a temporary tooth restoration.

4. The system of claim 3, wherein the material is a bis-acrylic material or a bis-acrylic composite material.

5. The system of claim 1, wherein the male relief feature comprises a longitudinal protrusion, and wherein the female relief feature comprises a longitudinal slot.

6. The system of claim 1, wherein the abutment further comprises at least one retention feature disposed around an outer peripheral surface of the component supporting portion, the at least one retention feature extending in a direction transverse to the longitudinal axis of the abutment, and
   wherein the temporary coping further comprises at least one complimentary retention feature configured for snap-fit engagement with the at least one retention feature.

7. The system of claim 1, wherein the component supporting portion further comprises a plurality of retention features spaced from one another around an outer peripheral surface of the component supporting portion, the retention features being disposed at a common axial location along a length of the abutment and extending in a direction transverse to the longitudinal axis of the abutment, and
   wherein the temporary coping further comprises a plurality of complimentary retention features configured for engagement with the plurality of retention features.

8. The system of claim 6, wherein the at least one retention feature comprises at least one retention groove, and wherein the at least one complimentary retention feature comprises at least one protrusion.

9. The system of claim 7, wherein the plurality of retention features comprises a plurality of retention grooves, and
   wherein the plurality of complimentary retention features comprises a plurality of protrusions.

10. The system of claim 1, wherein the apical end surface of the coping comprises an angled surface.

11. The system of claim 1, wherein the apical end surface of the coping comprises a convex end surface.

12. The system of claim 1, wherein the apical end surface of the coping comprises an angled edge.

13. The system of claim 1, wherein the apical end surface of the coping comprises a groove.

14. The system of claim 1, wherein the male relief feature extends along the entire length of the flat surface portion of the abutment, and wherein the female relief feature extends along the entire length of the flat surface portion of the coping.

15. The system of claim 1, wherein the male relief feature is disposed centrally between lateral sides defining the flat surface portion of the abutment, and wherein the female relief feature is disposed centrally between lateral sides defining the flat surface portion of the coping.

* * * * *

UNITED STATES PATENT AND TRADEMARK OFFICE
CERTIFICATE OF CORRECTION

| | | |
|---|---|---|
| PATENT NO. | : 8,920,170 B2 | Page 1 of 1 |
| APPLICATION NO. | : 13/401349 | |
| DATED | : December 30, 2014 | |
| INVENTOR(S) | : Anatoli Krivoruk | |

It is certified that error appears in the above-identified patent and that said Letters Patent is hereby corrected as shown below:

In the Claims

Col. 21, Claim 3, line 2, replace the word "boding" with --bonding--.

Signed and Sealed this
Nineteenth Day of May, 2015

Michelle K. Lee
*Director of the United States Patent and Trademark Office*